US010881723B2

United States Patent
Onuma et al.

(10) Patent No.: US 10,881,723 B2
(45) Date of Patent: *Jan. 5, 2021

(54) VACCINE CONTAINING IMMOBILIZED VIRUS PARTICLES

(71) Applicant: KM BIOLOGICS CO., LTD., Kumamoto (JP)

(72) Inventors: Hiroto Onuma, Kikuchi (JP); Yukari Tsurudome, Kikuchi (JP); Kazuyuki Ikeda, Kikuchi (JP); Ryo Yamaue, Kikuchi (JP); Kazuhiko Kimachi, Kikuchi (JP); Motoharu Abe, Kikuchi (JP); Akihiro Watanabe, Kikuchi (JP); Yuki Ohara, Kikuchi (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 4 days.

This patent is subject to a terminal disclaimer.

(21) Appl. No.: 16/066,664

(22) PCT Filed: Jan. 10, 2017

(86) PCT No.: PCT/JP2017/000485
§ 371 (c)(1),
(2) Date: Jun. 27, 2018

(87) PCT Pub. No.: WO2017/122635
PCT Pub. Date: Jul. 20, 2017

(65) Prior Publication Data
US 2019/0000960 A1    Jan. 3, 2019

(30) Foreign Application Priority Data
Jan. 15, 2016  (JP) .................. 2016-006133

(51) Int. Cl.
*A61K 39/12* (2006.01)
*A61K 39/145* (2006.01)
(Continued)

(52) U.S. Cl.
CPC ............ *A61K 39/145* (2013.01); *A61K 31/12* (2013.01); *A61K 31/16* (2013.01); *A61K 39/12* (2013.01);
(Continued)

(58) Field of Classification Search
None
See application file for complete search history.

(56) References Cited

U.S. PATENT DOCUMENTS 6,149,917 A * 11/2000 Fanget .................. A61P 31/12
424/218.1
2002/0001595 A1   1/2002 Sonntag et al.
2017/0196965 A1* 7/2017 Kimachi ................ A61K 39/12

FOREIGN PATENT DOCUMENTS

CA         2955287 A1    1/2016
CN       104498446 A    4/2015
(Continued)

OTHER PUBLICATIONS

Barteling et al. Formaldehyde Inactivation of Foot-And-Mouth Disease Virus. Conditions for the Preparation of Safe Vaccine. Arch Virol. 1984;80(2-3):103-17. (Year: 1984).*
(Continued)

*Primary Examiner* — Michelle S Horning
(74) *Attorney, Agent, or Firm* — Pillsbury Winthrop Shaw Pittman, LLP

(57) ABSTRACT

The present invention relates to a vaccine containing fixed virus particles, wherein a summed fever response of three rabbits to the fixed virus particles in a pyrogen test is less than 80% based on a summed fever response of three rabbits
(Continued)

to original virus particles of the fixed virus particles or corresponding inactivated virus particles.

19 Claims, 6 Drawing Sheets

(51) Int. Cl.
    *A61P 31/16*     (2006.01)
    *A61K 31/12*     (2006.01)
    *A61K 31/16*     (2006.01)
    *A61P 31/12*     (2006.01)
    *A61K 39/00*     (2006.01)

(52) U.S. Cl.
    CPC ............... *A61P 31/12* (2018.01); *A61P 31/16* (2018.01); *A61K 2039/5252* (2013.01); *C12N 2760/16134* (2013.01); *Y02A 50/30* (2018.01)

(56) References Cited

FOREIGN PATENT DOCUMENTS

| | | | |
|---|---|---|---|
| EP | 3170509 A1 | 5/2017 | |
| JP | 2002-528422 A | 9/2002 | |
| JP | 2003-517834 A | 6/2003 | |
| JP | 2010-0514817 A | 5/2010 | |
| WO | 99/11762 A1 | 3/1999 | |
| WO | 01/46390 A2 | 6/2001 | |
| WO | 01/076624 A1 | 10/2001 | |
| WO | WO-2008073490 A1 * | 6/2008 | ............. A61K 39/12 |
| WO | 2008/081014 A2 | 7/2008 | |
| WO | 2016/010081 A1 | 1/2016 | |

OTHER PUBLICATIONS

Delrue et al. Inactivated virus vaccines from chemistry to prophylaxis: merits, risks and challenges. Expert Rev. Vaccines 11(6), 695-719 (2012) (Year: 2012).*

Patent Cooperation Treaty, International Preliminary Report on Patentability for PCT/JP2017/000485, dated Jul. 26, 2018, pp. 1-12.

Patent Cooperation Treaty, International Search Report for PCT/JP2017/000485 (translated), dated Feb. 21 2017, pp. 1-3.

Delrue et al., Inactivated virus vaccines from chemistry to prophylaxis: merits, risks and challenges, Expert Review of Vaccines, 2012, pp. 695-719, vol. 11(6).

Szymczakiewicz-Multanowska et al., Safety and Immunogenicity of a Novel Influenza Subunit Vaccine Produced in Mammalian Cell Culture, The Journal of Infectious Diseases, 2009, pp. 841-848, vol. 200(6).

Groth et al., Safety, tolerability and immunogenicity of a mammalian cell-culture-derived influenza vaccine: A sequential Phase I and Phase II clinical trial, Vaccine, Jan. 29, 2009, pp. 786-791, vol. 27(5).

European Patent Office, Supplementary Partial European Search Report issued in EP Application No. 17738389.0, dated Oct. 24, 2019, pp. 1-14.

Rappuoli et al., Toxin inactivation and antigen stabilization: two different uses of formaldehyde, Vaccine, Elsevier, Amsterdam, NL, Jan. 1, 1994, pp. 579-581, vol. 12, No. 7.

Clausi et al., Formulation approach for the development of a stable, lyophilized formaldehyde-containing vaccine, European Journal of Pharmaceutics and Biopharmaceutics, Elsevier Science Publishers B.V., May 11, 2013, pp. 272-278, vol. 85, No. 2, Amsterdam, NL.

European Patent Office, Extended European Search Report issued in EP Application No. 17738389.0, dated Mar. 23, 2020, pp. 1-13.

Watanabe et al., "Efficacy of chemically cross-linked antigens for acellular pertussis vaccine", Vaccine, Elsevier, Dec. 8, 2000, pp. 1199-1203, vol. 19(9-10), Amsterdam, NL.

Christodoulides et al., "Optimal conditions for the toxoiding of pertussis toxin with 1-ethyl-3 (3-dimethylaminopropyl) carbodiimide. HC1", FEMS Microbiology Letters, Dec. 1, 1989, pp. 425-435, vol. 47(8-9), Wiley-Blackwell Publishing Ltd, GB.

Gajendra Sunnamada Naika et al, "Purification and Characterization of a New Endoglucanase from Aspergillus aculeatus", Journal of Agricultural and Food Chemistry, Sep. 1, 2007, pp. 7566-7572, vol. 55(18).

Taiwan Intellectual Property Office, Office Action issued in corresponding TW Patent Application No. 106101131, dated May 29, 2020, p. 19, English translation of cited references.

* cited by examiner

VACCINE CONTAINING IMMOBILIZED VIRUS PARTICLES

CROSS-REFERENCE TO RELATED APPLICATIONS

This patent application is a national stage entry of, and claims priority to International Patent Application No. PCT/JP2017/000485 filed Jul. 10, 2017, and published on Jul. 20, 2017, as International Patent Publication WO/2017/122635, which claims priority to Japanese Patent Application No. JP 2016-006133 filed Jan. 15, 2016, the contents of each of these applications being incorporated herein by reference in their entireties.

TECHNICAL FIELD

The present invention relates to a vaccine containing fixed virus particles. More specifically, the present invention relates to a vaccine containing fixed virus particles with adverse reactions suppressed by fixing the particle structure of the virus in a fixative.

BACKGROUND ART

Infectious diseases by viruses such as influenza virus and Japanese encephalitis virus may become severe depending on the kinds of the viruses or infected subjects. Vaccination or the like is known as a method for defense or prevention against such infectious diseases by viruses.

CITATION LIST

Patent Literature

Patent Literature 1: International Publication No. WO 2016/010081

Non Patent Literature

Non Patent Literature 1: J. Infect. Dis. 2009 200 (6) 841-848
Non Patent Literature 2: Vaccine 2009 27 (5) 786-791

SUMMARY OF INVENTION

Problems to be Solved by the Invention

Vaccines against viruses such as influenza virus and Japanese encephalitis virus are produced and commercially available as two kinds: inactivated vaccines and live vaccines. Among them, the inactivated vaccines were broadly divided into whole virus vaccines which are prepared by treating purified virus particles with an inactivator such as formalin, and split virus vaccines which are prepared by disrupting (splitting) purified virus particles with an organic solvent or a surfactant. The whole virus vaccines have high immunogenicity and are excellent in terms of an effect of preventing infections. However, the whole virus vaccines have the tendency that adverse reactions such as local responses and fever responses are strongly manifested. On the other hand, the split virus vaccines are excellent in safety because local responses are reduced and few fever responses are present. However, the immunogenicity of the split virus vaccines tends to be low in children whose basic immunity has not yet been established or elderly people whose immune responses are weakened. Thus, the development of vaccines that exhibit better efficacy (immunogenicity) than that of the split virus vaccines and have high safety is demanded.

The present invention has been made in light of the situation described above, and an object thereof is to provide a vaccine whose immunogenicity is high and adverse reactions are suppressed.

Means for Solving the Problems

The present inventors have conducted diligent studies to attain the object and consequently completed the present invention by finding that, surprisingly, a vaccine containing virus particles (hereinafter, also referred to as "fixed virus particles") that maintain a component and a structure equivalent to original virus particles by fixing the particle structure of the virus particles in a fixative without disruption (splitting) is equivalent in an immunogenicity test and excellent in the results of a pyrogen test, etc. about adverse reactions.

Specifically, the present invention provides the following [1] to [15]:

[1] A vaccine containing fixed virus particles, wherein a summed fever response of three rabbits to the fixed virus particles in a pyrogen test is less than 80% based on a summed fever response of three rabbits to original virus particles of the fixed virus particles or corresponding inactivated virus particles.

[2] The vaccine according to [1], wherein the summed fever response of three rabbits to the fixed virus particles in the pyrogen test is 1.3° C. or lower.

[3] A vaccine containing fixed virus particles, wherein an amount of an inflammatory cytokine produced from human peripheral blood mononuclear cells stimulated with the fixed virus particles is less than 80% based on an amount of the inflammatory cytokine produced from human peripheral blood mononuclear cells stimulated with original virus particles of the fixed virus particles or corresponding inactivated virus particles.

[4] The vaccine according to any of [1] to [3], wherein the original virus particles of the fixed virus particles comprise orthomyxovirus particles, flavivirus particles, or picornavirus particles.

[5] The vaccine according to [4], wherein the virus particles comprise influenza virus particles, Japanese encephalitis virus particles, or hepatitis A virus particles.

[6] The vaccine according to [5], wherein the virus particles comprise influenza virus particles.

[7] The vaccine according to [6], wherein the influenza virus particles comprise influenza A virus particles or influenza B virus particles.

[8] The vaccine according to [6] or [7], wherein the influenza virus particles comprise influenza virus particles classified into a strain of H1N1 subtype, a strain of H2N2 subtype, a strain of H3N2 subtype, a strain of H3N8 subtype, a strain of H5N1 subtype, a strain of H5N2 subtype, a strain of H5N6 subtype, a strain of H6N1 subtype, a strain of H7N3 subtype, a strain of H7N7 subtype, a strain of H7N9 subtype, a strain of H9N2 subtype, or a strain of H10N8 subtype.

[9] The vaccine according to [5], wherein the virus particles comprise Japanese encephalitis virus particles.

[10] The vaccine according to [9], wherein the Japanese encephalitis virus particles comprise a Beijing-1 strain, a Nakayama strain, a SA14-14-2 strain, or a P3 strain.

[11] The vaccine according to any of [1] to [10], wherein 0% to 90% of a surface protein on the fixed virus particles is unfixed.

[12] The vaccine according to any of [1] to [11], wherein a relative value of specific activity (antigen content/protein content) of the fixed virus particles to specific activity of the original virus particles of the fixed virus particles is 0% to 95%.

[13] The vaccine according to any of [1] to [12], wherein the fixed virus particles have a mean particle size of 80% to 150% of particle sizes of the original virus particles of the fixed virus particles or the corresponding inactivated virus particles.

[14] The vaccine according to any of [1] to [13], wherein a peak is detected at a sucrose concentration of 35% or higher when the fixed virus particles are measured by sucrose density gradient cocentrifugation.

[15] The vaccine according to any of [1] to [14], wherein a single peak is observed when the fixed virus particles are measured by high-performance liquid chromatography.

[16] The vaccine according to any of [1] to [15], wherein the vaccine induces the fixed virus particle-specific IgG2a rather than the fixed virus particle-specific IgG1 when immunizing a mouse.

The present invention further provides the following [17] to [31]:

[17] A method for producing fixed virus particles, comprising the step of adding a fixative to a suspension containing original virus particles or corresponding inactivated virus particles.

[18] The production method according to [17], wherein the fixative comprises an aldehyde.

[19] The production method according to [18], wherein the aldehyde is selected from the group consisting of formaldehyde, paraformaldehyde, glutaraldehyde, and combinations thereof.

[20] The production method according to [19], wherein the aldehyde comprises formaldehyde.

[21] The production method according to [20], wherein a concentration of the formaldehyde is 0.005 to 0.5 w/v % based on the total amount of the suspension and the fixative.

[22] The production method according to [19], wherein the aldehyde comprises glutaraldehyde.

[23] The production method according to [22], wherein a concentration of the glutaraldehyde is 0.001 to 0.06 w/v % based on the total amount of the suspension and the fixative.

[24] The production method according to [17], wherein the fixative comprises a carbodiimide.

[25] The production method according to [24], wherein the carbodiimide is selected from the group consisting of dicyclohexylcarbodiimide, diisopropylcarbodiimide, 1-ethyl-3-(3-dimethylaminopropyl)carbodiimide hydrochloride, analogs thereof and combinations thereof.

[26] The production method according to [25], wherein the carbodiimide comprises 1-ethyl-3-(3-dimethylaminopropyl)carbodiimide hydrochloride.

[27] The production method according to [26], wherein a concentration of the 1-ethyl-3-(3-dimethylaminopropyl)carbodiimide hydrochloride is 0.05 to 1500 mM based on the total amount of the suspension and the fixative.

[28] The production method according to any of [17] to [27], wherein the original virus particles are virus particles recovered by infecting cultured cells, a chicken egg or the mouse brain.

[29] The production method according to [28], wherein the cultured cells comprise primary cells or cell lines.

[30] The production method according to [29], wherein the cultured cells comprise Vero cells or MDCK cells.

[31] A method for producing a vaccine, comprising the step of adding fixed virus particles obtained by a production method according to any of [17] to [30].

Effects of the Invention

According to the present invention, it is possible to provide a vaccine whose immunogenicity is high and adverse reactions are suppressed.

EMBODIMENTS FOR CARRYING OUT THE INVENTION

Figure 1:
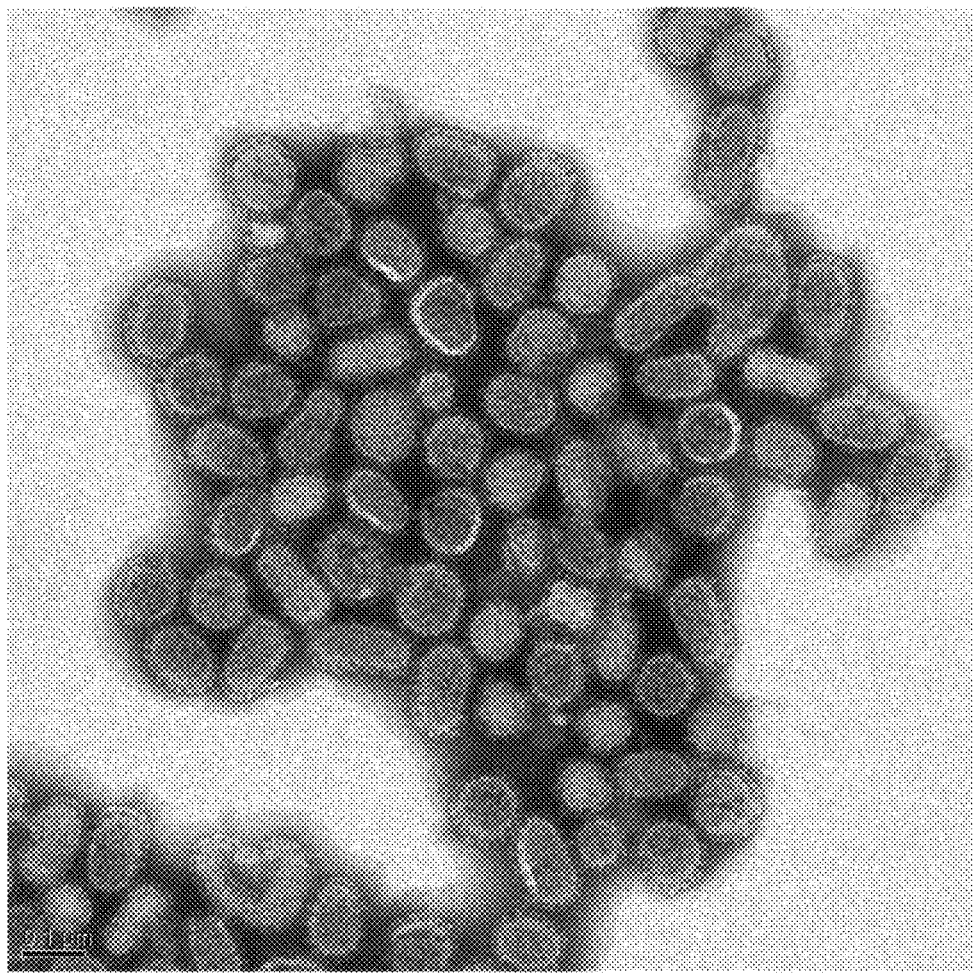
FIG. 1 is a photograph of fixed influenza virus particles photographed under an electron microscope (formalin treatment).

Hereinafter, preferable embodiments of the present invention will be described in detail. However, the present invention is not limited by the following embodiments.

(Vaccine Containing Fixed Virus Particles)

The vaccine according to the present embodiment is a vaccine containing fixed virus particles, wherein the summed fever response (° C.) of three rabbits to the fixed virus particles in a pyrogen test is reduced based on the summed fever response of three rabbits to original virus particles of the fixed virus particles or corresponding inactivated virus particles. Also, in the vaccine, the amount of an inflammatory cytokine produced from human peripheral blood mononuclear cells stimulated with the fixed virus particles is reduced based on the amount of the inflammatory cytokine produced from human peripheral blood mononuclear cells stimulated with original virus particles of the fixed virus particles or corresponding inactivated virus particles. Namely, the immunogenicity of the vaccine containing fixed virus particles is equal to or larger than the immunogenicity of a split virus vaccine, and adverse reactions such as local responses and fever responses are kept equivalent to the split virus vaccine. In another aspect, the fixed virus particles are excellent in stability as compared with a whole virus vaccine containing conventional inactivated virus particles.

The "fixed virus particles" mean virus particles that lack the ability to infect a host and whose particle structure is fixed by cross-linking the surface proteins of the virus particles to each other. Since the fixed virus particles maintain particulate equivalent to original virus particles or corresponding inactivated virus particles, the immunogenicity is high. The fixed virus particles are obtained by treating original virus particles or corresponding inactivated virus particles with a fixative. In this context, the "fixative" means an agent that cross-links the proteins of the virus particles to each other through covalent bonds. For example, the fixative is an agent that cross-links surface antigens to each other, a surface antigen to a matrix protein or a membrane protein, matrix proteins to each other, or membrane proteins to each other and retains the particle structure of the virus particles.

The "inactivated virus particles" mean virus particles that lack the ability to infect a host and whose particle structure is unfixed. The inactivated virus particles are obtained by treating original virus particles with an inactivator. In the case of influenza virus particles, the inactivated virus particles may be, for example, one obtained by adding formalin (36 to 38 w/v % aqueous formaldehyde solution) to a suspension containing the influenza virus particles such that the final concentration becomes 0.02 v/v % (0.0072 to 0.0076 w/v % in terms of formaldehyde), and reacting at 4° C. for 6 weeks. In the case of Japanese encephalitis virus particles, the inactivated virus particles may be, for example, a commercially available Vero cell culture Japanese encephalitis bulk vaccine (manufactured by General Incorporated Foundation, The Chemo-Sero-Therapeutic Research Institute, trade name "ENCEVAC", containing Japanese encephalitis virus particles already inactivated with 0.08 v/v % formalin).

The pyrogen test is conducted by a method conforming to a pyrogen test method shown in Japanese Minimum Requirements for Biological Products (Ministry of Health, Labour and Welfare Ministerial Notification No. 192). The "fever response" means the maximum value of the difference (also referred to as a "differential rectal temperature") between the rectal temperature of a rabbit measured after injection of a specimen into the ear vein (also referred to as a "measurement value") and the rectal temperature of the rabbit measured before the injection (also referred to as a "control rectal temperature"). In this context, when the differential rectal temperature is a negative value, the fever response is interpreted as 0.

Specifically, the pyrogen test is conducted by the following procedures: first, one in which the protein content in 1 mL is adjusted to 70 μg (in the case of Japanese encephalitis virus particles) or 240 μg (in the case of influenza virus particles) by diluting the fixed virus particles with saline is used as a sample. 1 to 3 mL of the sample per kg of body weight is inoculated to rabbits, and elevation in rectal temperature is observed up to 6 hours later. The difference between the rectal temperature (control rectal temperature) of a rabbit before the inoculation of the sample and the rectal temperature of the rabbit after the inoculation is determined, and the maximum value of the difference is used as the fever response of the rabbit. The same test is conducted for three rabbits, and the summed fever response (° C.) of the three rabbits is determined.

In the vaccine, the summed fever response of three rabbits to the fixed virus particles in the pyrogen test may be less than 80%, may be less than 60%, may be less than 40%, may be less than 20%, and may be less than 10%, based on the summed fever response of three rabbits to original virus particles of the fixed virus particles or corresponding inactivated virus particles. The lower limit is not particularly limited, but may be 0% or more and may be 20% or more, based on the summed fever response of three rabbits to original virus particles of the fixed virus particles or corresponding inactivated virus particles. By setting the summed fever response to the range described above, it is possible to provide a vaccine whose adverse reactions are suppressed as compared with a whole virus vaccine containing conventional inactivated virus particles.

In the vaccine, the summed fever response of three rabbits to the fixed virus particles in the pyrogen test may be 1.3° C. or lower, may be 0.9° C. or lower, and may be 0.5° C. or lower. The lower limit is not particularly limited, but may be 0° C. or higher and may be 0.6° C. or higher. By setting the summed fever response to the range described above, it is possible to provide a vaccine whose adverse reactions are suppressed as compared with a whole virus vaccine containing conventional inactivated virus particles.

The "inflammatory cytokine" is a generic name for cytokines that are produced in response to inflammation, and examples include IL-1β, IL-6, TNF-α, IFN-α, and IFN-γ.

The "human peripheral blood mononuclear cells" (PBMC) mean lymphocytes (including T cells, B cells, NK cells, etc.) and monocytes obtained from human peripheral blood.

The amount of the inflammatory cytokine is determined by determining the amount of the inflammatory cytokine produced in the case of stimulating human peripheral blood mononuclear cells (PBMC) with the virus particles by a method conforming to the European Pharmacopoeia Monocyte-Activation Test. The method described above may be a method for the European Pharmacopoeia Monocyte-Activation Test subjected to change in measurement conditions shown in Examples mentioned later.

In the vaccine, the amount of an inflammatory cytokine produced from human peripheral blood mononuclear cells stimulated with the fixed virus particles may be less than 80%, may be less than 60%, may be less than 40%, may be less than 20%, and may be less than 10%, based on the amount of the inflammatory cytokine produced from human peripheral blood mononuclear cells stimulated with original virus particles of the fixed virus particles or corresponding inactivated virus particles. The lower limit is not particularly limited, but may be 0% or more and may be 40% or more, based on the amount of the inflammatory cytokine produced from human peripheral blood mononuclear cells stimulated with original virus particles of the fixed virus particles or corresponding inactivated virus particles. By setting the amount of an inflammatory cytokine produced from human peripheral blood mononuclear cells stimulated with the fixed virus particles to the range described above, it is possible to provide a vaccine whose adverse reactions are suppressed as compared with a whole virus vaccine containing conventional inactivated virus particles.

In the case where the inflammatory cytokine is IL-1β, the concentration of the inflammatory cytokine produced from human peripheral blood mononuclear cells stimulated with the fixed virus particles may be 30 pg/ml or lower and may be 20 pg/ml or lower, based on a culture solution containing the human peripheral blood mononuclear cells. The lower limit is not particularly limited, but may be 0 pg/ml or higher and may be 5 pg/ml or higher. By setting the concentration of the inflammatory cytokine produced from human peripheral blood mononuclear cells stimulated with the fixed virus particles to the range described above, it is possible to provide a vaccine whose adverse reactions are suppressed as compared with a whole virus vaccine containing conventional inactivated virus particles.

In the case where the inflammatory cytokine is IL-6, the concentration of the inflammatory cytokine produced from human peripheral blood mononuclear cells stimulated with the fixed virus particles may be 50 pg/ml or lower and may be 40 pg/ml or lower, based on a culture solution containing the human peripheral blood mononuclear cells. The lower limit is not particularly limited, but may be 0 pg/ml or higher and may be 5 pg/ml or higher. By setting the concentration of the inflammatory cytokine produced from human peripheral blood mononuclear cells stimulated with the fixed virus particles to the range described above, it is possible to provide a vaccine whose adverse reactions are suppressed as compared with a whole virus vaccine containing conventional inactivated virus particles.

Examples of the original virus particles of the fixed virus particles include poxvirus particles, herpesvirus particles, orthomyxovirus particles, paramyxovirus particles, rhabdovirus particles, coronavirus particles, arenavirus particles, togavirus particles, flavivirus particles, bunyavirus particles, retrovirus particles, hepadnavirus particles, adenovirus particles, papillomavirus particles, papovavirus particles, filovirus particles, reovirus particles, picornavirus particles and calicivirus particles. Examples of the orthomyxovirus particles include influenza virus particles. Examples of the flavivirus particles include Japanese encephalitis virus particles. Examples of the picornavirus particles include hepatitis A virus particles.

Examples of the influenza virus particles include influenza A virus particles and influenza B virus particles. Examples of the influenza A virus particles include influenza particles classified into a strain of H1N1 subtype, a strain of H2N2 subtype, a strain of H3N2 subtype, a strain of H3N8 subtype, a strain of H5N1 subtype, a strain of H5N2 subtype, a strain of H5N6 subtype, a strain of H6N1 subtype, a strain of H7N3 subtype, a strain of H7N7 subtype, a strain of H7N9 subtype, a strain of H9N2 subtype, or a strain of H10N8 subtype.

Examples of the Japanese encephalitis virus particles include Japanese encephalitis virus particles of a Beijing-1 strain, a Nakayama strain (Nakayama-NIH strain), a SA14-14-2 strain, and a P3 strain.

The fixed virus particles contains genomic nucleic acids (DNA, RNA, etc.) derived from the virus particles because unlike a split virus vaccine, the particle structure is not disrupted. The virus particle-derived genomic nucleic acids are capable of acting as adjuvants. For example, inactivated poliovirus vaccines include D antigen containing viral genomic RNA and C antigen free from viral genomic RNA. The C antigen has weak immunogenicity and does not exhibit an effect as a vaccine antigen. A molecular species having an effect as a vaccine antigen is only the D antigen. This suggests that viral genomic RNA enclosed in a vaccine is important for the exertion of its effect. Therefore, the vaccine according to the present embodiment is capable of inducing a Th1-type response. It is contrast with a split influenza virus vaccine which induces a Th2-type response. An antibody of IgG2a subclass induced by the Th1-type response in mice is superior in the ability to defend against infection by influenza virus to an antibody of IgG1 subclass induced by the Th2-type response. From this, further improvement in efficacy by the vaccine can be expected. Namely, when immunizing a mouse, the vaccine may induce IgG2a which is specific for the fixed virus particles rather than IgG1 which is specific for the fixed virus particles.

The fixed virus particles may have a parameter (e.g., molecular weight, mean particle size, density, or hemagglutinin (HA) content) substantially identical to the original virus particles or the corresponding inactivated virus particles, when measured by sucrose density gradient centrifugation, high-performance liquid chromatography, and/or a dynamic light scattering method.

For example, the fixed virus particles may be fixed virus particles having a mean particle size of 80% to 150% of the particle sizes of the original virus particles or the corresponding inactivated virus particles and may be fixed virus particles having a mean particle size of 90% to 140%. In the case of Japanese encephalitis virus particles, the fixed virus particles may be fixed virus particles having a mean particle size of 90% to 130% of the particle sizes of the original virus particles or the corresponding inactivated virus particles and may be fixed virus particles having a mean particle size of 100% to 120%.

In the case where the fixed virus particles originate in influenza virus particles, the mean particle size of the fixed virus particles may be around 150 nm, may be 120 nm to 180 nm, and may be 130 nm to 170 nm, when measured by the dynamic light scattering method. In another aspect, in the case where the fixed virus particles originate in influenza virus particles, the mean particle size of the fixed virus particles may be 100 nm or larger, may be 120 nm or larger, may be 130 nm or larger, may be 150 nm or larger, and may be 170 nm or larger, when measured by the dynamic light scattering method. The mean particle size may be 180 nm or smaller, may be 175 nm or smaller, and may be 170 nm or smaller. In the case where the fixed virus particles originate in Japanese encephalitis virus particles, the mean particle size of the fixed virus particles may be around 90 nm and may be 80 nm to 110 nm, when measured by the dynamic light scattering method. In another aspect, in the case where the fixed virus particles originate in Japanese encephalitis virus particles, the mean particle size of the fixed virus particles may be 70 nm or larger, may be 80 nm or larger, and may be 90 nm or larger, when measured by the dynamic light scattering method. The mean particle size may be 110 nm or smaller and may be 100 nm or smaller.

In the case where the fixed virus particles originate in virus particles having an envelope, the content of a lipid component in the fixed virus particles may be equivalent to the content of the lipid component in the virus particles described above.

The fixed virus particles may be fixed virus particles in which a peak is detected at a sucrose concentration of 35% or higher, and may be fixed virus particles in which a peak is detected at a sucrose concentration of 45% or higher and 55% or lower, when measured by the sucrose density gradient centrifugation. It is possible that the sucrose concentration is determined by a publicly known method. For example, the sucrose concentration can be determined by overlaying a specimen containing the fixed virus particles on a sucrose density gradient from 15 to 60%, and performing centrifugation at 18000 rpm (RCF=57500 (×g)) for 16 hours at 4° C.

The fixed virus particles may be fixed virus particles in which a single peak is observed when measured by the high-performance liquid chromatography (size exclusion chromatography (SEC)). For example, in the case of performing molecular weight measurement using size exclusion chromatography (trade name: TSKgel G6000PWXL (manufactured by Tosoh Corp.) or Superose 6 10/300 GE (manufactured by GE Healthcare Japan Corp.)) (eluent: PBS, flow rate: 0.5 ml/min), they may be fixed virus particles of Japanese encephalitis virus particles in which a single peak is observed at an elution time around 14 to 15 minutes, and may be fixed virus particles of influenza virus particles in which a single peak is observed at an elution time around 16 to 17 minutes.

In the vaccine, 0% to 90% of a surface protein on the fixed virus particles may be unfixed, and 5% to 80% of a surface protein on the fixed virus particles may be unfixed.

Examples of the surface protein on the fixed virus particles include surface antigens, matrix proteins, membrane proteins, and combinations thereof.

In the case where the virus particles are influenza virus particles, examples of the surface antigens include hemagglutinin (HA) and neuraminidase (NA). Examples of the matrix proteins include M1 protein. Examples of the membrane proteins include M2 protein.

In the case where the virus particles are Japanese encephalitis virus particles, examples of the surface antigens include E protein and M protein.

Examples of the method for calculating the ratio of an unfixed protein include a method of determining percent change (residual rate) in the amount of the protein between before fixation and after fixation for the original molecular weight of the target protein. In the case where the fixed virus particles originate in influenza virus particles, examples include a method of performing SDS-PAGE (polyacrylamide gel electrophoresis) under reductive conditions, then determining the density of the band of the M1 protein, one of the constituent proteins of the virus, by densitometry, and calculating the residual rate (%) of the M1 protein. In this case, as the concentration of the fixative increases, the residual rate of the M1 protein tends to decrease. By applying this method, the analysis of the degree of cross-linking by the fixative can be conducted.

In the present embodiment, in the case where the fixed virus particles originate in influenza virus particles, they may be fixed virus particles in which the residual rate of the M1 protein is 5% to 90%, and may be fixed virus particles in which the residual rate of the M1 protein is 10% to 80%. In other words, 5% to 90% of the M1 protein may be unfixed, and 10% to 80% may be unfixed.

The analysis of the degree of cross-linking can also be conducted by determining the specific activity (antigen content/protein content) of the fixed virus particles. A monoclonal antibody that is used in the antigen content measurement of the virus particles recognizes a neutralizing epitope, and the specific activity decreases when the structural change of the neutralizing epitope occurs. A relative value (%) of the specific activity of the fixed virus particles to the unfixed virus particles is calculated by utilizing this property, and the degree of cross-linking is evaluated. In the present embodiment, the relative value of the specific activity is in the range of 0 to 95%. In the case where the fixed virus particles originate in Japanese encephalitis virus, the relative value of the specific activity of the fixed Japanese encephalitis virus particles may be 90 to 95%, may be 70 to 90%, and may be 50 to 70%.

The amount of the fixed virus particles contained in the vaccine may be appropriately selected according to the kind of the virus or a recipient. For example, the amount (concentration) of the fixed virus particles contained in an influenza vaccine may be 1 to 40 μg of HA/mL as a hemagglutinin concentration per virus strain.

The vaccine may be a monovalent vaccine containing an antigen derived from the same kind of virus or bacterium. The vaccine may be a combined vaccine containing antigens derived from a plurality of kinds of viruses or bacteria. The vaccine may be a multivalent vaccine containing antigens derived from viruses or bacteria of the same genus and of a plurality of kinds of types. For example, in the case where the vaccine is an influenza virus vaccine, it may contain either fixed influenza A virus particles or fixed influenza B virus particles or may contain both of them. In the case where the vaccine is a Japanese encephalitis virus vaccine, it may contain either a cell culture-derived or mouse brain-derived virus. The influenza virus vaccine or the Japanese encephalitis virus vaccine may contain an antigen derived from an additional virus or bacterium. For example, it may be mixed with diphtheria-pertussis-tetanus-inactivated poliovirus combined vaccine (DPT-IPV vaccine).

The dosage form of the vaccine may be, for example, a liquid form, a powder form (lyophilized powder, dried powder, etc.), a capsule form, a tablet, or a frozen state.

The vaccine may contain a pharmaceutically acceptable carrier. A carrier that is usually used in vaccine production can be used as the carrier described above without limitations. Specifically, examples of the carrier include saline, buffered saline, dextrose, water, glycerol, isotonic aqueous buffer solutions and combinations thereof. The vaccine may be further appropriately supplemented with an emulsifier, a preservative (e.g., thimerosal), a tonicity agent, a pH adjuster, an inactivator (e.g., formalin), and the like.

The administration route of the vaccine may be, for example, transdermal administration, sublingual administration, eye drop administration, intradermal administration, intramuscular administration, oral administration, enteral administration, intranasal administration, intravenous administration, subcutaneous administration, intraperitoneal administration, and inhalation administration from the mouth to the lung.

The method for administering the vaccine may be, for example, a method of performing administration through a syringe, a transdermal patch, a microneedle, a transplantable sustained-release device, a syringe equipped with a microneedle, a needless apparatus, or a spray.

In order to further enhance immunogenicity, the vaccine may contain an adjuvant. Examples of the adjuvant include aluminum adjuvants or squalene-containing oil-in-water emulsion adjuvants (AS03, MF59, etc.), ligands of Toll-like receptors such as CpG and 3-O-desacyl-4'-monophosphoryl lipid A (MPL), saponin-based adjuvants, polymer-based adjuvants such as poly-γ-glutamic acid, and polysaccharides such as chitosan and inulin.

Examples of the target mammal include mice, rats, guinea pigs, hamsters, rabbits, cats, dogs, sheep, pigs, cattle, horses, goats, monkeys, and humans. The vaccine according to the present embodiment may be used for humans and may be used for children under the age 5 and 65-year-old or older elderly people.

In the case where an influenza vaccine is administered to a human, the vaccine may be used such that 3.8 μg of HA to 30 μg of HA per dose of the active ingredient (fixed virus particles) is administered, though differing depending on the purpose of administration, the administration method, and the condition of the recipient (sex, age, body weight, medical condition, etc.).

(Method for Producing Fixed Virus Particles)

The method for producing fixed virus particles according to the present embodiment comprises the step of fixing a particle structure for original virus particles or corresponding inactivated virus particles.

Methods for disrupting (splitting) virus particles having an envelope by using a surfactant or an organic solvent have heretofore been known as techniques of enhancing the safety of vaccines. However, in these methods, the efficacy (immunogenicity) of vaccines tends to decrease in association with the collapse of the particles. In the production method described above, the virus particle structure is maintained, and consequently, it is possible to enhance safety while maintaining the efficacy of the vaccine, because of treating the original virus particles or the corresponding inactivated virus particles with a fixative that causes covalent bonds with virus particle proteins.

The production method may further comprise the step of culturing a host, the step of allowing the virus to infect the host, the step of replicating the virus within the host, the step of recovering virus particles from the host, or the step of inactivating the recovered virus particles.

The virus particles may be virus particles recovered from a host after the virus particles are allowed to infect the host and replicated. The host may be appropriately selected according to the kind of the virus particles. The method for inactivating the virus particles can employ a publicly known method, and examples include a method of performing inactivation with an inactivator such as formalin. In the case where the virus particles are influenza virus particles, examples of the host include cultured cells, chicken eggs and the mouse brain. The cultured cells may be primary cells or cell lines. Examples of the cultured cells include Vero cells and MDCK cells.

A method using a chicken egg or Vero cells as a host (Vaccine, 1998 May-June; 16 (9-10): 960-8), a method using Vero cells as a host (Vaccine, 2007 Aug. 10; 25 (32): 6028-6036), and a method using MDCK cells as a host (J Virol. 2012 November; 86 (22): 12341-50) are methods known to those skilled in the art as infection and replication methods of influenza virus.

Fixation of Virus Particles

Examples of the fixation step include the method of treating original virus particles or corresponding inactivated virus particles with a fixative, and examples include the step of adding a fixative to a suspension containing original virus particles or corresponding inactivated virus particles. The concentration of the virus particles in the suspension may be appropriately changed according to the kind of the virus, the kind of the fixative and the concentration thereof, etc. For example, the concentration of the virus particles in the suspension may be 60 to 90 µg/mL, may be 300 to 3000 µg/mL, and may be 500 to 2500 µg/mL, as the protein concentration of the virus particles.

The kind of the fixative can be appropriately changed according to the kind of the virus. Examples of the fixative include organic solvents, aldehydes, diimidoester, bis(3,5-dibromosalicyl) fumarate (DBBF), carbodiimides, and combinations thereof. Examples of the organic solvents include methanol, ethanol, acetone, and combinations thereof. Examples of the aldehydes include formaldehyde (FA) (e.g., formalin), paraformaldehyde, glutaraldehyde (GA), and combinations thereof. Examples of the carbodiimides include dicyclohexylcarbodiimide (DCC), diisopropylcarbodiimide (DIC), 1-ethyl-3-(3-dimethylaminopropyl)carbodiimide hydrochloride (EDC), analogs thereof and combinations thereof.

The concentration of the fixative may be appropriately changed according to the kind of the virus and the kind of the fixative. In the case where the fixative comprises formaldehyde, the concentration of the formaldehyde may be 0.005 to 0.5 w/v % based on the total amount of the suspension containing the virus particles and the fixative. In the case where the concentration of the formaldehyde is less than 0.005 w/v %, there is the tendency that the fixation becomes weak and the particle structure is difficult to retain. In the case where the concentration of the formaldehyde exceeds 0.5 w/v %, there is the tendency that the fixation is strong and chemical modification by cross-linking proceeds too much. From the viewpoint of further improving HA titer, the concentration of the formaldehyde may be 0.01 to 0.5 w/v %, may be 0.018 to 0.152 w/v %, may be 0.029 to 0.152 w/v %, and may be 0.029 to 0.076 w/v %, based on the total amount of the suspension and the fixative. The method using the fixative comprising formaldehyde may be used in the case where the virus particles are influenza virus particles or Japanese encephalitis virus particles.

In the case where the fixative is formalin (36 to 38 w/v % aqueous formaldehyde solution), the formalin concentration may be 0.014 to 0.4 v/v %, may be 0.05 to 0.4 v/v %, may be 0.08 to 0.4 v/v %, and may be 0.08 to 0.2 v/v %, based on the total amount of the suspension and the fixative.

In the case where the fixative comprises glutaraldehyde, the concentration of the glutaraldehyde may be 0.001 to 0.06 w/v %, may be 0.002 to 0.05 w/v %, may be 0.004 to 0.02 w/v %, and may be 0.005 to 0.01 w/v %, based on the total amount of the suspension and the fixative. In the case where the concentration is less than 0.001 w/v %, the particles tend to aggregate when Japanese encephalitis virus particles are used as the virus particles. In the case where the concentration exceeds 0.06 w/v %, the epitope of E protein which is a major structural protein tends to be inactivated when Japanese encephalitis virus particles are used as the virus particles. The method using glutaraldehyde as the fixative may be used in the case where the virus particles are influenza virus particles or Japanese encephalitis virus particles.

In the case where the fixative comprises EDC, the concentration of the EDC may be 0.05 to 1500 mM, may be 0.15 to 500 mM, and may be 5 to 50 mM, based on the total amount of the suspension and the fixative. The method using the fixative comprising EDC may be used in the case where the virus particles are influenza virus particles or Japanese encephalitis virus particles.

The temperature at the time of the treatment with the fixative may be appropriately changed according to the kind of the virus, the kind of the fixative, the concentration of the fixative, etc. The temperature may be 0° C. (ice bath) to 37° C., may be 4° C. to 37° C., and may be 25° C. to 37° C.

The period at the time of the treatment with the fixative (treatment time) may be appropriately changed according to the kind of the virus, the kind of the fixative, the concentration of the fixative, the temperature of the treatment, etc. The period may be 1 day to 4 weeks, may be 3 days to 4 weeks, and may be 1 week to 4 weeks. In the case of using EDC as the fixative, the period may be 5 minutes to 24 hours, may be 0.5 hours to 24 hours, and may be 2 hours to 20 hours.

In order to terminate the progression of cross-linking by the fixative, quenching treatment may be performed by using an amino acid such as glycine. The quenching treatment may be performed for the purpose of improvement in the stability, immunogenicity, and safety of the vaccine.

According to the need, the step of purifying the recovered fixed virus particles may be further comprised. Although it is possible to appropriately perform the method for purifying the fixed virus particles by a publicly known method, examples include a method of performing filtration by using an ultrafiltration membrane.

The method for producing a vaccine according to the present embodiment comprises the step of adding fixed virus particles obtained by the method for producing fixed virus particles. The method for producing a vaccine may further comprise the step of adding a pharmaceutically acceptable carrier, an emulsifier, a preservative, a tonicity agent, a pH adjuster, an inactivator, and the like.

It is preferable for vaccination to be able to impart the quality and quantity of immunization similar to those at the time of actual infection, to a subject, and the mimicking properties of immunity induced by a vaccine against immunity caused by actual infection determines its effect. All virus proteins may be contained as antigens for defense against infection in the vaccine. Considering that the presence of virus-derived genomic nucleic acids for enhancing the immunogenicity of the virus proteins, the size and shape of the virus particles, etc. each individually work for immune responses, the present inventors believe that the best vaccine is one having a component and a structure more similar to those of the actual virus. Since the fixed virus particles according to the present embodiment have a component and a structure equivalent to original virus particles except that mere fixation with a fixative, it becomes possible to provide a vaccine whose immunogenicity is high and adverse reactions are suppressed.

EXAMPLES

Although the present invention will be described below in detail with reference to Examples, the present invention is not limited by these Examples by any means.

Example 1

1. Preparation of Antigen Derived from Influenza Virus Particles (1) Preparation of FA-Fixed Influenza Virus Particles Formaldehyde (FA) Treatment An influenza A virus strain of H1N1 subtype (A/California/07/2009 (X-179A) strain; hereinafter, also referred to as an "A/CA strain") was inoculated into the allantoic cavities of 11-day-old embryonated eggs and cultured at 34° C. for 2 days. After the obtained allantoic fluid was clarified, influenza virus particles were precipitated by ultracentrifugation. The influenza virus particles were resuspended in phosphate-buffered saline (PBS) to obtain a suspension. The obtained suspension was centrifuged by sucrose density gradient centrifugation (RCF=57500 (×g), 16 hr), and the influenza particles were purified by recovering a fraction having a sucrose concentration of 33% to 50%. The obtained fraction was diluted such that the final protein concentration of the purified influenza virus particles became 500 μg/mL, to obtain a suspension. Then, formalin (36 to 38 w/v % aqueous formaldehyde solution) was added to the suspension such that the final concentration became 0.05 to 0.20 v/v % (0.018 to 0.076 w/v % in terms of formaldehyde), and reacted at 25° C. for 1 week. After the completion of reaction, formaldehyde was removed by dialyzing the reaction solution against PBS, to thereby obtain fixed influenza virus particles (hereinafter, also referred to as "FA-fixed influenza virus particles").

(2) Preparation of Inactivated Influenza Virus Particles

Formalin (36 to 38 w/v % aqueous formaldehyde solution) was added to the suspension such that the final concentration became 0.02 v/v % (0.0072 to 0.0076 w/v % in terms of formaldehyde), and reacted at 4° C. for 6 weeks to 8 weeks. After the completion of reaction, formaldehyde was removed by dialyzing the reaction solution against PBS, to thereby obtain inactivated influenza virus particles. Inactivated influenza virus particles were also prepared as to other influenza virus strains (subtype strains) by a similar method and used as comparative controls in Examples 1 to 6.

(3) Preparation of Split Influenza Virus Antigen

A split influenza virus antigen (hereinafter, also referred to as a "split flu antigen") as a comparative control employed a stock solution of each strain contained in an influenza HA vaccine (manufactured by General Incorporated Foundation, The Chemo-Sero-Therapeutic Research Institute, trade name "influenza HA vaccine "KAKETSUKEN"").

2. Pyrogen Test

The pyrogen test was conducted according to Japanese Minimum Requirements for Biological Products (Ministry of Health, Labour and Welfare Ministerial Notification No. 192). One in which the protein content in 1 mL was adjusted to 240 μg by diluting the inactivated influenza virus particles, the FA-fixed influenza virus particles or the split flu antigen with saline was used as a sample. 1 to 3 mL of the sample per kg of body weight was inoculated to rabbits, and elevation in rectal temperature was observed up to 6 hours later. The difference between the rectal temperature (control rectal temperature) of a rabbit before the inoculation of the sample and the rectal temperature of the rabbit after the inoculation was determined, and the maximum value of the difference was used as the fever response of the rabbit. The same test was conducted for three rabbits. The summed fever response (° C.) of the three rabbits is shown in Table 1.

TABLE 1

| A/CA strain (strain of H1N1 subtype): Summed fever response of three rabbits | | |
|---|---|---|
| | Formalin concentration (v/v %) | Summed fever response (° C.) |
| FA-fixed influenza virus particles | 0.05 | 0.30 |
| | 0.08 | 0.51 |
| | 0.11 | 0.20 |
| | 0.14 | 0.17 |
| | 0.20 | 0.04 |
| Inactivated influenza virus particles | — | 3.72 |
| Split flu antigen | — | 0.53 |

For all of the FA-fixed influenza virus particles, a summed fever response of 1.3° C. or higher was not observed, and 3° C. or more decrease in summed fever response was seen as compared with the inactivated influenza virus particles. It was found for the FA-fixed influenza virus particles that the summed fever response was sufficiently low, as in the split flu antigen. Also from this, it was suggested that the FA-fixed influenza virus particles have high safety, as in the split flu antigen.

3. Determination of Amount of Inflammatory Cytokine Produced

The amount of an inflammatory cytokine (IL-6) produced in the case of stimulating human peripheral blood mononuclear cells (PBMC) with the FA-fixed influenza virus particles whose fixation was performed at a formalin concentration of 0.05 v/v %, 0.08 v/v %, or 0.11 v/v % or the inactivated influenza virus particles was determined by a method conforming to the European Pharmacopoeia Monocyte-Activation Test. Specifically, the human PBMC is used by pooling that from at least 4 donors in the European Pharmacopoeia Monocyte-Activation Test, but was changed to that from 1 donor and measured. The results about the amount of the cytokine produced against the FA-fixed influenza virus particles and the inactivated influenza virus particles are shown in Table 2. It was found that the amount of IL-6 produced for the FA-fixed influenza virus particles is sufficiently low as compared with the inactivated influenza virus particles. From this, it was suggested that the FA-fixed influenza virus particles have high safety as compared with the inactivated influenza virus particles.

TABLE 2

A/CA strain (strain of H1N1 subtype): Amount of inflammatory cytokine produced

|  | Formalin concentration (v/v %) | IL-6 (pg/mL) |
|---|---|---|
| FA-fixed influenza virus particles | 0.05 | 9.2 |
|  | 0.08 | 7.3 |
|  | 0.11 | 9.2 |
| Inactivated influenza virus particles | — | 17.0 |

Example 2

Physical Evaluation

1. Analysis by Sucrose Density Gradient Centrifugation Method

The obtained fraction was diluted by a method conforming to Example 1 described above such that the final protein concentration of the influenza virus particles (A/CA strain) became 2500 μg/mL, to obtain a suspension. Then, formalin was added to the suspension such that the final concentration became 0.12 v/v %, and reacted at 25° C. for 1 week. FA-fixed influenza virus particles were obtained by dialyzing the reaction solution with PBS. The obtained FA-fixed influenza virus particles were analyzed by the sucrose density gradient centrifugation method. A specimen was overlaid on a sucrose density gradient from 15 to 60%, and centrifugation was performed at 18000 rpm (57500 (×g)) for 16 hours at 4° C. After the centrifugation, fractionation was performed into 0.6 mL per fraction, and the sucrose concentration, HA titer and protein concentration of each fraction were measured. The results about the A/CA strain (strain of H1N1 subtype) are shown in Table 3. It was shown for the split flu antigen that the proteins were broadly distributed over sucrose concentrations from 25 to 50%, and the virus particles were degraded. In contrast to this, it was shown for the FA-fixed influenza virus particles to be fractionated as a single peak (particulate) at a high sucrose concentration (44.3%). The HA titer was 10240 times.

TABLE 3

A/CA strain (strain of H1N1 subtype): Sucrose density gradient centrifugation analysis and HA titer

|  | FA-fixed influenza virus particles | Split flu antigen |
|---|---|---|
| Sucrose concentration (%) | 44.3 Single peak | 25-50 Broad distribution |
| Protein content (μg/mL) | 460.0 | — |
| HA titer (x) | 10240 | — |

2. Analysis Under Electron Microscope

In order to examine the shape of the FA-fixed influenza virus particles (A/CA strain) in more detail, observation under an electron microscope was carried out. A specimen was fixed by using glutaraldehyde at room temperature for 20 minutes. Then, the fixed specimen was placed on an ion-coated sheet mesh for observation (manufactured by Nisshin EM Co., Ltd.), left standing for approximately 60 seconds, and negatively stained with a 2% aqueous phosphotungstic acid solution. The stained specimen was observed and photographed by using a transmission electron microscope (Tecnai G2 manufactured by FEI Company; accelerating voltage: 120 kV).

The photograph of the FA-fixed influenza virus particles photographed under the electron microscope is shown in FIG. 1. The FA-fixed influenza virus particles maintained the particle structure, as in the inactivated influenza virus particles.

3. Dynamic Light Scattering

FA-fixed influenza virus particles originating in an influenza A virus strain of H3N2 subtype (A/New York/39/2012 (X-233A) strain; hereinafter, also referred to as an "A/NY strain") and an influenza B virus Victoria lineage strain (B/Brisbane/60/2008 strain; hereinafter, also referred to as a "B/BR strain") were prepared by a method conforming to Example 1, and their respective mean particle sizes were analyzed by using Zetasizer Nano ZS (manufactured by Malvern Panalytical Ltd.). The mean particle sizes in a liquid by the dynamic light scattering method are shown in Table 4. The FA-fixed influenza virus particles had a mean particle size around 140 to 150 nm which was single. From this, it was found that the mean particle size of the FA-fixed influenza virus particles is equivalent to the inactivated influenza virus particles. The particle structure of the FA-fixed influenza virus particles was maintained, and impurities such as aggregates were not observed.

TABLE 4

Mean particle size in liquid by dynamic light scattering method (volume-weighted mean particle size (main peak) (nm))

| Strain name of original virus particles | FA-fixed influenza virus particles | Inactivated influenza virus particles |
|---|---|---|
| A/NY strain (strain of H3N2 subtype) | 139.5 | 159.2 |
| B/BR strain (strain of B type) | 149.3 | 137.8 |

4. Molecular Weight Distribution Measurement (SEC)

FA-fixed influenza virus particles (B/MA strain) were prepared as to an influenza B virus Yamagata lineage strain (B/Massachusetts/02/2012 (BX-51B) strain (hereinafter, also referred to as a "B/MA strain")) by a method conforming to Example 1 described above. The molecular weight distribution measurement of the split flu antigen and the FA-fixed influenza virus particles was performed as to an A/CA strain (strain of H1N1 subtype), an A/NY strain (strain of H3N2 subtype), and the B/MA strain (strain of B type) by using size exclusion chromatography (trade name: TSKgel G6000PWXL (manufactured by Tosoh Corp.)) (performed at a flow rate of 0.5 ml/min by using PBS as an eluent). The elution pattern thereof is shown in Table 5. For the FA-fixed influenza virus particles, a single peak was observed at an elution time around 16 to 17 minutes. On the other hand, for the split flu antigen derived from the same strain, three peaks were observed at an elution time around 19 to 30 minutes.

TABLE 5

SEC elution pattern (elution time (min))

| Strain name of original virus particles | FA-fixed influenza virus particles | Split flu antigen |
|---|---|---|
| A/CA strain (strain of H1N1 subtype) | 16-17 Single peak | 19, 26, 30 Three peaks |
| A/NY strain (strain of H3N2 subtype) | 16-17 Single peak | 19, 24, 26 Three peaks |
| B/MA strain (strain of B type) | 16-17 Single peak | 19, 24, 25 Three peaks |

5. Analysis by Degree of Cross-Linking

The degree of cross-linking by the fixative was analyzed as to the FA-fixed influenza virus particles (A/CA strain) prepared in Example 1 by the following procedures: after SDS-Buffer (final concentration: 0.76 w/v % Tris, 1 w/v % SDS, 10 v/v % glycerol, 0.01 w/v % bromophenol blue (BPB)) and 2-mercaptoethanol (final concentration: 0.8 v/v %) were first added to a specimen and boiled for 6 minutes, SDS-PAGE was performed by using PAGEL NPU-12.5L (manufactured by ATTO Technology, Inc., trade name) or PAGEL NPU-R12.5L (manufactured by ATTO Technology, Inc., trade name). After the electrophoresis, CBB (Coomassie brilliant blue) staining was performed, and images were captured with LAS3000 (manufactured by FUJIFILM Corp., trade name). As cross-linking by the fixative proceeds, M1 protein, one of the proteins constituting the virus, shifts from the original band position (25 to 37 kDa) to higher molecular weights. Therefore, it is suggested that the band of the M1 protein (M1 band) detected at the original position gets light, which was used as an index for the degree of cross-linking Specifically, the relative value (%) of the densitometry value of the M1 band detected at the original position (hereinafter, this relative value is also referred to as a "M1 protein residual rate" (%)), of the FA-fixed influenza virus particles treated at each formalin concentration to the densitometry value of the M1 band of the unfixed influenza virus particles was calculated. The results are shown in Table 6. The M1 protein residual rates of the FA-fixed influenza virus particles (A/CA strain) whose fixation was performed at formalin concentrations of 0.05%, 0.08%, 0.11%, and 0.14% were 35.7%, 23.8%, 11.0%, and 5.4%, respectively, suggesting that as the formalin concentration increases, cross-linking is accelerated so that the M1 protein residual rate decreases.

TABLE 6

A/CA strain (strain of H1N1 subtype): M1 protein residual rate

| | Formalin concentration (v/v %) | M1 protein residual rate (%) |
|---|---|---|
| FA-fixed influenza virus particles | 0.05 | 35.7 |
| | 0.08 | 23.8 |
| | 0.11 | 11.0 |
| | 0.14 | 5.4 |

6. Immunogenicity-1 (Mouse Intramuscular Inoculation)

The immunogenicity of the FA-fixed influenza virus particles (A/CA strain) was evaluated by using mice. The split flu antigen, the inactivated influenza virus particles, or the FA-fixed influenza virus particles (A/CA strain) were intramuscularly inoculated at an inoculum dose of 0.8 μg as the amount of proteins to ddY mice (female, 8 weeks old) (13 animals per group). Three weeks after the immunization, the mice were subjected to the collection of whole blood and euthanized. Serum was obtained by centrifugation, and the HI titer was measured according to "Pathogen Detection Manual" (edited by National Institute of Infectious Diseases, Japan). The results about immunogenicity (HI titer (GMT)) when the intramuscular inoculation was performed for the mice are shown in Table 7. The FA-fixed influenza virus particles (A/CA strain) had high immunogenicity as compared with the split flu antigen and had immunogenicity equivalent to the inactivated influenza virus particles.

TABLE 7

| A/CA strain (strain of H1N1 subtype): HI titer (GMT) (mouse intramuscular inoculation) | | | |
|---|---|---|---|
| | FA-fixed influenza virus particles | Inactivated influenza virus particles | Split flu antigen |
| GMT | 65 | 65 | 36 |

7. Immunogenicity-2 (Mouse Intradermal Inoculation)

The immunogenicity of the FA-fixed influenza virus particles (A/CA strain) was evaluated by mouse intradermal inoculation by the same procedures as in "6. Immunogenicity-1 (mouse intramuscular inoculation)" described above. The split flu antigen, the inactivated influenza virus particles, or the FA-fixed influenza virus particles were intradermally inoculated at an inoculum dose of 0.2 μg as the amount of proteins to ddY mice (female, 8 weeks old) (5 animals per group). Three weeks after the immunization, the mice were subjected to the collection of whole blood and euthanized. Serum was obtained by centrifugation, and the HI titer was measured. The results about immunogenicity (HI titer (GMT)) when the intradermal inoculation was performed for the mice are shown in Table 8. The FA-fixed influenza virus particles had significantly high immunogenicity as compared with the split flu antigen and had immunogenicity equivalent to the inactivated influenza virus particles.

TABLE 8

| A/CA strain (strain of H1N1 subtype): HI titer (GMT) (mouse intradermal inoculation) | | | |
|---|---|---|---|
| | FA-fixed influenza virus particles | Inactivated influenza virus particles | Split flu antigen |
| GMT | 106*1 | 106*1 | 30 |

*1 $p < 0.05$

8. Immunogenicity-3 (Cynomolgus Monkey Subcutaneous Inoculation)

The immunogenicity of the split flu antigen, the inactivated influenza virus particles, and the FA-fixed influenza virus particles was evaluated as to an A/CA strain (strain of H1N1 subtype), an A/NY strain (strain of H3N2 subtype), and a B/BR strain and a B/MA strain (strains of B type) by using cynomolgus monkeys (male or female, 17 to 25 months old). The split flu antigen, the inactivated influenza virus particles, or the FA-fixed influenza virus particles were subcutaneously inoculated twice at a 21-day interval at an inoculum dose corresponding to 7.5 μg of HA (the amount of proteins corresponding to the amount of HA of the split flu antigen) to 8 or 9 animals per group. Before the secondary immunization and on day 21 after the secondary immunization, the collection of partial blood was performed. Serum was obtained by centrifugation, and the HI titer and the neutralizing titer were measured according to "Pathogen Detection Manual" (edited by National Institute of Infectious Diseases, Japan). The results about immunogenicity are shown in Table 9 (HI titer (GMT) on day 21 after secondary immunization) and Table 10 (neutralizing titer (GMT) on day 21 after secondary immunization). It was found for the HI titer that the FA-fixed influenza virus particles have high immunogenicity as compared with the split flu antigen. Particularly, the immunogenicity, excluding the B/MA strain, was significantly high as compared with the split flu antigen. As for the neutralizing titer, the FA-fixed influenza virus particles also had significantly high immunogenicity for all the strains of A type and the strains of B type as compared with the split flu antigen.

TABLE 9

HI titer (GMT): Cynomolgus monkey subcutaneous inoculation (day 21 after secondary immunization)

| | FA-fixed influenza virus particles | Inactivated influenza virus particles | Split flu antigen |
|---|---|---|---|
| A/CA strain (strain of H1N1 subtype) | 160*[1] | 226*[2] | 18 |
| A/NY strain (strain of H3N2 subtype) | 34*[1] | 37*[1] | 11 |
| B/BR strain (strain of B type) | 52*[2] | 31*[2] | 8 |
| B/MA strain (strain of B type) | 18 | 20*[2] | 5 |

*[1]$p < 0.05$,
*[2]$p < 0.01$

TABLE 10

Neutralizing titer (GMT): Cynomolgus monkey subcutaneous inoculation (day 21 after secondary immunization)

| | FA-fixed influenza virus particles | Inactivated influenza virus particles | Split flu antigen |
|---|---|---|---|
| A/CA strain (strain of H1N1 subtype) | 761*[2] | 1076*[2] | 62 |
| A/NY strain (strain of H3N2 subtype) | 698*[1] | 640*[1] | 135 |
| B/BR strain (strain of B type) | 174*[2] | 147*[2] | 18 |
| B/MA strain (strain of B type) | 174*[2] | 174*[2] | 14 |

*[1]$p < 0.05$,
*[2]$p < 0.01$

9. Antibody Subclass Analysis

The titers of virus antigen-specific IgG1 and IgG2a contained in the mouse serum were measured as to an A/CA strain (strain of H1N1 subtype) and a B/MA strain (strain of B type) obtained in "6. Immunogenicity-1 (mouse intramuscular inoculation)" described above by the enzyme-linked immunosorbent assay (ELISA) method as antibody subclass analysis. As a result, it was shown that the FA-fixed influenza virus particles induce antigen-specific IgG2a rather than antigen-specific IgG1 (Tables 11 and 12). This is a result similar to that of the inactivated influenza virus particles, and stronger tendency to induce IgG2a was also seen in the comparison with the split flu antigen. From this result, the FA-fixed influenza virus particles can be expected to further improve the efficacy of a vaccine as compared with the split flu antigen which activates humoral immunity but can hardly activate cell-mediated immunity.

TABLE 11

A/CA strain (strain of H1N1 subtype): Results of subclass analysis (EU/mL)

| IgG subclass | FA-fixed influenza virus particles | Inactivated influenza virus particles | Split flu antigen |
|---|---|---|---|
| IgG1 | 200 | 280 | 7108 |
| IgG2a | 13997 | 18248 | 9351 |

A value when the serum of each mouse immunized with the split flu antigen was diluted 25600-fold was defined as 1 EU/mL.

TABLE 12

B/MA strain (Yamagata lineage strain): Results of subclass analysis (EU/mL)

| IgG subclass | FA-fixed influenza virus particles | Inactivated influenza virus particles | Split flu antigen |
|---|---|---|---|
| IgG1 | 200 | 498 | 2694 |
| IgG2a | 15853 | 8867 | 3622 |

A value when the serum of each mouse immunized with the split flu antigen was diluted 25600-fold was defined as 1 EU/mL.

10. Evaluation of Amount of RNA Released

The amount of RNA released over time during protease treatment was evaluated as to FA-fixed influenza virus particles (A/NY strain) prepared by a method conforming to Example 1, by the following procedures: first, the FA-fixed influenza virus particles were diluted with PBS, and SDS and proteinase K were added, and reacted at 55° C. while RNA was extracted over time. TRIzol LS Reagent, PureLink RNA Mini Kit, and PureLink DNase (manufactured by Invitrogen Corp., trade name) were used in the RNA extraction. The content of the extracted RNA was measured with Quant-iT RiboGreen RNA Reagent and Kit (manufactured by Invitrogen Corp., trade name). The RNA content over time at each FA concentration is shown in Table 13. As a result, it was shown that RNA release is slowed in a FA concentration-dependent manner. It was suggested that the slowed RNA release by FA fixation slows inflammatory cytokine production, yielding high safety.

TABLE 13

Time-dependent change in content of RNA released after protease treatment

| | RNA content (ng/mL) | | | | |
|---|---|---|---|---|---|
| Protease treatment (hr) | 0.02% FA | 0.05% FA | 0.08% FA | 0.11% FA | 0.14% FA |
| 0.1 | 8 | 4 | 3 | 2 | 3 |
| 1.0 | 4424 | 2989 | 2205 | 1622 | 1284 |
| 6.0 | 5655 | 5462 | 5477 | 4795 | 4519 |
| 12.0 | 5513 | 6128 | 6447 | 5947 | 6385 |
| 18.0 | 6401 | 6525 | 6682 | 6794 | 6362 |
| 24.0 | 6187 | 6615 | 6902 | 6429 | 6555 |

Example 3

(1) Preparation of GA-Fixed Influenza Virus Particles

1. Glutaraldehyde (GA) Treatment

Influenza A virus (strain of H3N2 subtype (A/NY strain)) and influenza B virus (Victoria lineage strain of B type (B/BR strain)) were cultured and purified by the same method as in Example 1. The particles of each influenza virus purified were diluted such that the final protein concentration of the influenza virus particles became 1000 µg/mL, to obtain a suspension. Next, a 1 w/v % GA solution was used and diluted such that the GA concentration became 0.016 w/v % or 0.008 w/v %. The suspension and the diluted GA solution (0.016 w/v % or 0.008 w/v %) were mixed in equal amounts and reacted at 4° C. for 3 days. After the completion of reaction, GA was removed by dialyzing the reaction solution against PBS, to thereby obtain fixed influenza virus particles (hereinafter, also referred to as "GA-fixed influenza virus particles"). The pyrogenic activity of the obtained GA-fixed influenza virus particles (A/NY strain and B/BR strain) was evaluated by a pyrogen test of evaluating the summed fever response of three rabbits, and the determination of the amount of an inflammatory cytokine produced in the case of stimulating human PBMC.

2. Pyrogen Test

The pyrogen test was conducted by the same method as in Example 1. One in which the protein content in 1 mL was adjusted to 240 µg by diluting the inactivated influenza virus particles or the GA-fixed influenza virus particles (A/NY strain and B/BR strain) with saline was used as a sample. 1 mL of the sample per kg of body weight was inoculated to rabbits, and elevation in rectal temperature was observed up to 6 hours later. The summed fever response (° C.) of the three rabbits to the A/NY strain is shown in Table 14, and the summed fever response (° C.) of the three rabbits to the B/BR strain is shown in Table 15.

For all of the GA-fixed influenza virus particles, a summed fever response of 1.3° C. or higher was not observed, and 2.5° C. or more or 3° C. or more decrease in summed fever response based on the inactivated influenza virus particles was seen. It was found for the GA-fixed influenza virus particles that the summed fever response was sufficiently low. Also from this, it was suggested that the GA-fixed influenza virus particles have high safety as compared with the inactivated influenza virus particles.

TABLE 14

A/NY strain (strain of H3N2 subtype):
Summed fever response of three rabbits

|  | GA concentration (w/v %) | Summed fever response (° C.) |
| --- | --- | --- |
| GA-fixed influenza virus particles | 0.004 | 0.05 |
|  | 0.008 | 0.21 |
| Inactivated influenza virus particles | — | 2.78 |
| Split flu antigen | — | 0.05 |

TABLE 15

B/BR strain (Victoria lineage strain of B type):
Summed fever response of three rabbits

|  | GA concentration (w/v %) | Summed fever response (° C.) |
| --- | --- | --- |
| GA-fixed influenza virus particles | 0.004 | 0.00 |
|  | 0.008 | 0.20 |
| Inactivated influenza virus particles | — | 3.68 |
| Split flu antigen | — | 0.13 |

3. Determination of Amount of Inflammatory Cytokine Produced

The amount of a cytokine (IL-1β) produced in the case of stimulating human PBMC with the GA-fixed influenza virus particles or the inactivated influenza virus particles was determined by a method conforming to the European Pharmacopoeia Monocyte-Activation Test. Specifically, the human PBMC is used by pooling that from at least 4 donors in the European Pharmacopoeia Monocyte-Activation Test, but was changed to that from 1 donor and measured. The results about the amount of the cytokine produced against the GA-fixed influenza virus particles (A/NY strain and B/BR strain) are shown in Tables 16 and 17. It was found that the amount of the inflammatory cytokine produced for the GA-fixed influenza virus particles is sufficiently low as compared with the inactivated influenza virus particles. From this, it was suggested that the GA-fixed influenza virus particles have high safety, as in the split flu antigen.

TABLE 16

A/NY strain (strain of H3N2 subtype): Amount
of inflammatory cytokine produced

|  | GA concentration (w/v %) | IL-1β (pg/mL) |
| --- | --- | --- |
| GA-fixed influenza virus particles | 0.004 | 24.4 |
|  | 0.008 | 20.3 |
| Inactivated influenza virus particles | — | 41.3 |

TABLE 17

B/BR strain (Victoria lineage strain of B type):
Amount of inflammatory cytokine produced

|  | GA concentration (w/v %) | IL-1β (pg/mL) |
| --- | --- | --- |
| GA-fixed influenza virus particles | 0.004 | 20.9 |
|  | 0.008 | 16.4 |
| Inactivated influenza virus particles | — | 27.7 |

Example 4

Physical Evaluation

The physical properties of the GA-fixed influenza virus particles obtained in Example 3 described above were evaluated by the following methods.

1. Analysis Under Electron Microscope

Figure 2:
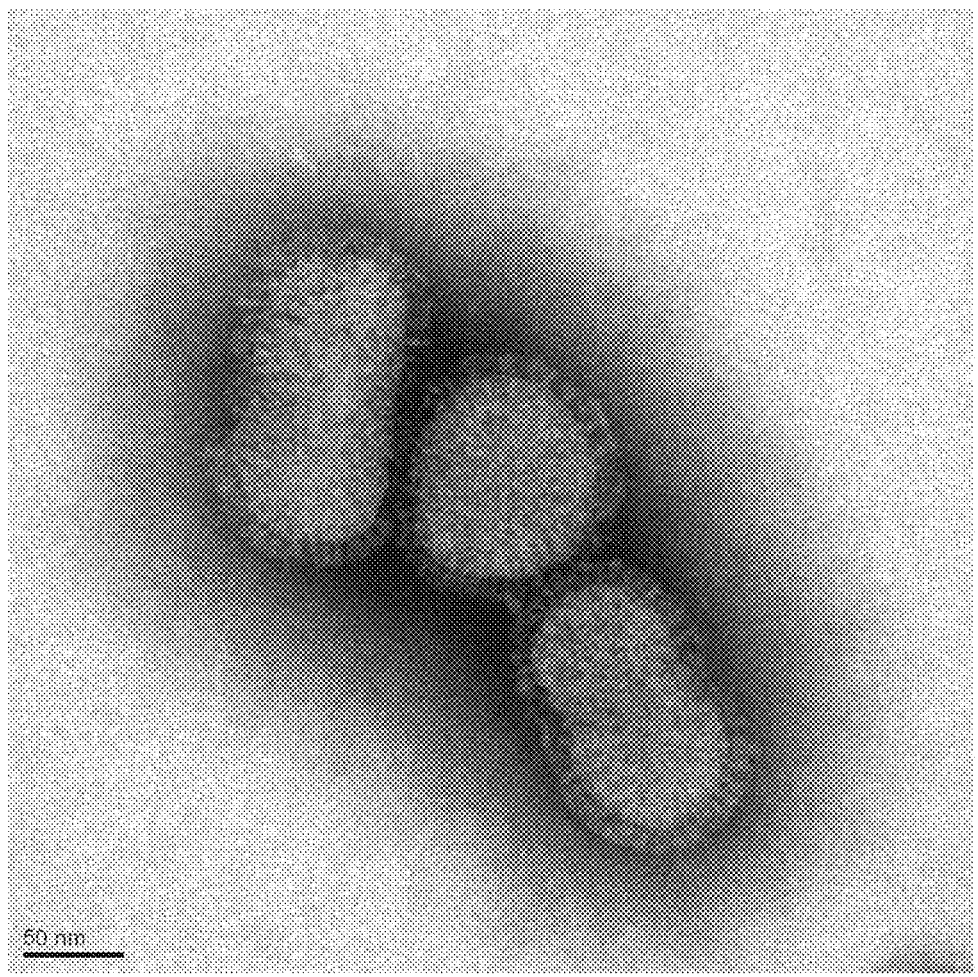
FIG. 2 is a photograph of fixed influenza virus particles photographed under an electron microscope (glutaraldehyde treatment).

In order to examine the shape of the GA-fixed influenza virus particles (A/NY strain) in more detail, observation under an electron microscope was carried out by the same method as in Example 2. As a representative, the photograph taken of the GA-fixed influenza virus particles (A/NY strain) reacted at 4° C. for 3 days at a GA concentration of 0.008 w/v % is shown in FIG. 2. The GA-fixed influenza virus particles maintained the particle structure, and aggregates in which particles were bound with each other were not observed.

2. Dynamic Light Scattering

The mean particle size of the GA-fixed influenza virus particles was analyzed by using Zetasizer Nano ZS (manufactured by Malvern Panalytical Ltd.). The mean particle size in a liquid by the dynamic light scattering method is shown in Table 18. The GA-fixed influenza virus particles had a mean particle size around 130 to 160 nm which was single. From this, it was found that the mean particle size of the GA-fixed influenza virus particles is equivalent to the original virus particles. Namely, it was found that the mean particle size of the GA-fixed influenza virus particles is single and is not variable. The particle structure of the GA-fixed influenza virus particles was maintained, and impurities such as aggregates were not observed.

TABLE 18

Mean particle size in liquid by dynamic light scattering method (volume-weighted mean particle size (main peak) (nm))

| Strain name of original virus particles | GA concentration (w/v %) | GA-fixed influenza virus particles |
| --- | --- | --- |
| A/NY strain (strain of H3N2 subtype) | 0.004 | 161.8 |
| | 0.008 | 158.2 |
| B/BR strain (strain of B type) | 0.004 | 136.0 |
| | 0.008 | 136.1 |

3. Molecular Weight Distribution Measurement (SEC)

The molecular weight distribution of the GA-fixed influenza virus particles was measured by the same method (SEC) as in Example 2. The elution pattern thereof is shown in Table 19. For the split flu antigen, four peaks were observed at an elution time around 16 to 30 minutes. On the other hand, for the GA-fixed influenza virus particles, a single peak was observed at an elution time around 16 to 17 minutes.

TABLE 19

SEC elution pattern (elution time (min))

| Strain name of original virus particles | Type of antigen | GA concentration (w/v %) | SEC elution time (min) |
| --- | --- | --- | --- |
| A/NY strain (strain of H3N2 subtype) | GA-fixed influenza virus particles | 0.004 | 16-17 Single peak |
| | | 0.008 | 16-17 Single peak |
| | Split flu antigen | — | 16, 19, 26, 29 Four peaks |
| B/BR strain (strain of B type) | GA-fixed influenza virus particles | 0.004 | 16-17 Single peak |
| | | 0.008 | 16-17 Single peak |
| | Split flu antigen | — | 16, 18, 25, 29 Four peaks |

4. Analysis by Degree of Cross-Linking

The degree of cross-linking of the GA-fixed influenza virus particles by the fixative was analyzed by the same method as in Example 2. The results about a B/BR strain (Victoria lineage strain of B type) are shown in Table 20. The M1 protein residual rates of the GA-fixed influenza virus particles whose fixation was performed at glutaraldehyde concentrations of 0.004 w/v % and 0.008 w/v % were 23.8% and 10.8%, respectively, showing that as the glutaraldehyde concentration increases, cross-linking is accelerated so that the M1 protein residual rate decreases.

TABLE 20

B/BR strain (Victoria lineage strain of B type): M1 protein residual rate

| | GA concentration (w/v %) | M1 protein residual rate (%) |
| --- | --- | --- |
| GA-fixed influenza virus particles | 0.004 | 23.3 |
| | 0.008 | 10.8 |

5. Immunogenicity (Mouse Intramuscular Inoculation)

The immunogenicity of the GA-fixed influenza virus particles (B/BR strain) was evaluated by the following procedures: first, the split flu antigen or the GA-fixed influenza virus particles were intramuscularly inoculated at an inoculum dose of 0.8 μg as the amount of proteins to ddY mice (female, 8 weeks old) (16 animals per group). Three weeks after the immunization, the mice were subjected to the collection of whole blood and euthanized. Serum was obtained by centrifugation, and the neutralizing titer was measured. As a representative, the results about the immunogenicity (neutralizing titer (GMT)) of the B/BR strain (Victoria lineage strain of B type) are shown in Table 21. In the case of the strain of B type, the GA-fixed influenza virus particles had high immunogenicity as compared with the split flu antigen.

TABLE 21

B/BR strain (Victoria lineage strain of B type): Neutralizing titer (GMT) (mouse intramuscular inoculation)

| | GA concentration (w/v %) | Neutralizing titer (GMT) |
| --- | --- | --- |
| GA-fixed influenza virus particles | 0.004 | 38 |
| | 0.008 | 35 |
| Split flu antigen | — | 27 |

6. Antibody Subclass Analysis

The titers of influenza virus antigen-specific IgG1 and IgG2a contained in the mouse serum obtained in "5. Immunogenicity (mouse intramuscular inoculation)" described above were measured by the ELISA method as antibody subclass analysis. As a result, it was shown that, in contrast to the split flu antigen, the GA-fixed influenza virus particles induce antigen-specific IgG2a rather than antigen-specific IgG1 (Table 22). This is a result similar to that of the inactivated influenza virus particles. From this result, the GA-fixed influenza virus particles can be expected to further improve the efficacy of a vaccine as compared with the split flu antigen which activates humoral immunity but can hardly activate cell-mediated immunity.

TABLE 22

B/BR strain (Victoria lineage strain of B type): Results of subclass analysis (EU/mL)

| IgG subclass | Split flu antigen | Inactivated influenza virus particles | GA-fixed influenza virus particles | |
|---|---|---|---|---|
| | | | 0.004 (w/v %) | 0.008% (w/v %) |
| IgG1 | 3788 | 382 | 243 | 200 |
| IgG2a | 749 | 20306 | 10901 | 10669 |

A value when the serum of each mouse immunized with the split flu antigen (IgG1) or virus-like particles (IgG2a) was diluted 25600-fold was defined as 1 EU/mL.

Example 5

(1) Preparation of EDC-Fixed Influenza Virus Particles 1. 1-Ethyl-3-[3-Dimethylaminopropyl]carbodiimide Hydrochloride (EDC) Treatment Influenza A virus (strain of H3N2 subtype (A/NY strain)) and influenza B virus (Victoria lineage strain B/BR strain) were cultured and purified in the same way as in Example 1. The obtained fraction was diluted such that the final protein concentration of the particles of each influenza virus purified became 2500 μg/mL for the A/NY strain and 500 μg/mL for the B/BR strain, to obtain a suspension. Next, an EDC solution was serially diluted into 0.1 to 4 M with PBS, added to the suspension such that the final concentration became 50 to 500 mM, and reacted for 2 to 20 hours under ice cooling (0° C.). After the completion of reaction, EDC was removed by dialyzing the reaction solution against PBS, to thereby obtain fixed influenza virus particles (hereinafter, also referred to as "EDC-fixed influenza virus particles"). The pyrogenic activity of the obtained EDC-fixed influenza virus particles (A/NY strain and B/BR strain) was evaluated by a pyrogen test of evaluating the summed fever response of three rabbits, and the determination of the amount of an inflammatory cytokine produced in the case of stimulating human PBMC.

2. Pyrogen Test

The pyrogen test was conducted by the same method as in Example 1. One in which the protein content in 1 mL was adjusted to 240 μg by diluting the EDC-fixed influenza virus particles with saline was used as a sample. The EDC-fixed influenza virus particles employed a specimen in which after reaction for 2 hours under ice cooling at an EDC concentration of 50 mM or 500 mM, the reaction solution was subjected to dialysis treatment with PBS (an EDC concentration of 5 mM was also carried out as to the A/NY strain). Also, a specimen in which after reaction at 4° C. for 20 hours at an EDC concentration of 5 mM, the reaction solution was subjected to dialysis treatment with PBS was also used as to the A/NY strain. 1 mL of the sample per kg of body weight was inoculated to rabbits, and elevation in rectal temperature was observed up to 6 hours later. The summed fever response (° C.) of the three rabbits is shown in Tables 23 and 24.

For the EDC-fixed influenza virus particles, a summed fever response of 1.3° C. or higher was not observed under all the EDC treatment conditions. Also from this, it was suggested that the EDC-fixed influenza virus particles have high safety, as in the split flu antigen.

TABLE 23

A/NY strain (strain of H3N2 subtype): Summed fever response of three rabbits

| | EDC concentration (mM) | EDC treatment (hr) | Summed fever response (° C.) |
|---|---|---|---|
| EDC-fixed influenza virus particles | 5 | 2 | 0.66 |
| | 5 | 20 | 0.86 |
| | 50 | 2 | 0.12 |
| | 500 | 2 | 0.53 |
| Inactivated influenza virus particles | — | — | 2.78 |
| Split flu antigen | | | 0.05 |

TABLE 24

B/BR strain (Victoria lineage strain of B type): Summed fever response of three rabbits

| | EDC concentration (mM) | EDC treatment (hr) | Summed fever response (° C.) |
|---|---|---|---|
| EDC-fixed influenza virus particles | 50 | 2 | 0.24 |
| | 500 | 2 | 0.50 |
| Inactivated influenza virus particles | — | — | 3.68 |
| Split flu antigen | — | — | 0.13 |

3. Determination of Amount of Inflammatory Cytokine Produced

The amounts of cytokines (IL-1β and IL-6) produced in the case of stimulating human PBMC with the EDC-fixed influenza virus particles or the inactivated influenza virus particles were determined by a method conforming to the European Pharmacopoeia Monocyte-Activation Test. Specifically, the human PBMC is used by pooling that from at least 4 donors in the European Pharmacopoeia Monocyte-Activation Test, but was changed to that from 1 donor and measured. The results about the amounts of the cytokines produced against the EDC-fixed influenza virus particles and the inactivated influenza virus particles of an A/NY strain and a B/BR strain are shown in Tables 25 and 26. It was found that the amounts of the inflammatory cytokines produced for the EDC-fixed influenza virus particles are sufficiently low as compared with the inactivated influenza virus particles. From this, it was suggested that the EDC-fixed influenza virus particles easily suppress adverse reactions as compared with the inactivated influenza virus particles.

TABLE 25

A/NY strain (strain of H3N2 subtype): Amount of inflammatory cytokine produced

| | EDC concentration (mM) | IL-1β (pg/mL) | IL-6 (pg/mL) |
|---|---|---|---|
| EDC-fixed influenza virus particles | 50 | 5.8 | 37.9 |
| | 500 | 12.7 | 65.2 |
| Inactivated influenza virus particles | — | 41.3 | 129.7 |

TABLE 26

B/BR strain (Victoria lineage strain of B type):
Amount of inflammatory cytokine produced

| | EDC concentration (mM) | IL-1β (pg/mL) | IL-6 (pg/mL) |
|---|---|---|---|
| EDC-fixed influenza virus particles | 50 | Less than 3.9 | 16.4 |
| | 500 | 13.5 | 125.7 |
| Inactivated influenza virus particles | — | 27.7 | 197.1 |

Example 6

Physical Evaluation

The physical properties of the EDC-fixed influenza virus particles obtained in Example 5 described above were evaluated by the following methods.

1. Analysis by Sucrose Density Gradient Centrifugation Method

The EDC-fixed influenza virus particles were analyzed by the sucrose density gradient centrifugation method by the same method as in Example 2. As a representative, the results about the EDC-fixed influenza virus particles (A/NY strain (strain of H3N2 subtype)) after reaction for 2 hours under ice cooling at an EDC concentration of 50 mM are shown in Table 27. It was shown for the split flu antigen that the proteins were broadly distributed over sucrose concentrations from 25 to 50%, and the virus particles were degraded. In contrast to this, it was shown for the EDC-fixed influenza virus particles to be fractionated as a single peak (particulate) at a high sucrose concentration (47.2%). The HA titer was 10240 times.

TABLE 27

A/NY strain (strain of H3N2 subtype): Sucrose density gradient centrifugation analysis and HA titer

| | EDC-fixed influenza virus particles | Split flu antigen |
|---|---|---|
| Sucrose concentration (%) | 47.2 Single peak | 25-50 Broad distribution |
| Protein content (µg/mL) | 494.0 | — |
| HA titer (x) | 10240 | — |

2. Analysis Under Electron Microscope

Figure 3:
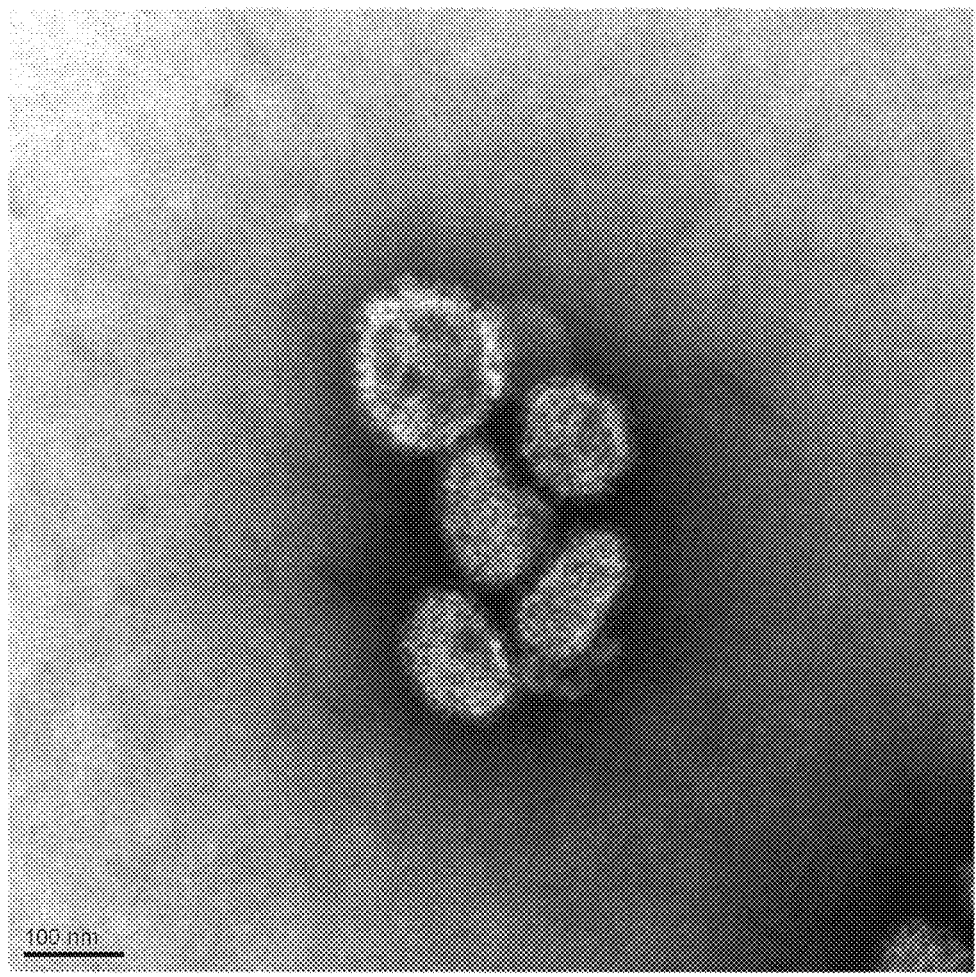
FIG. 3 is a photograph of fixed influenza virus particles photographed under an electron microscope (EDC treatment).
Figure 4:
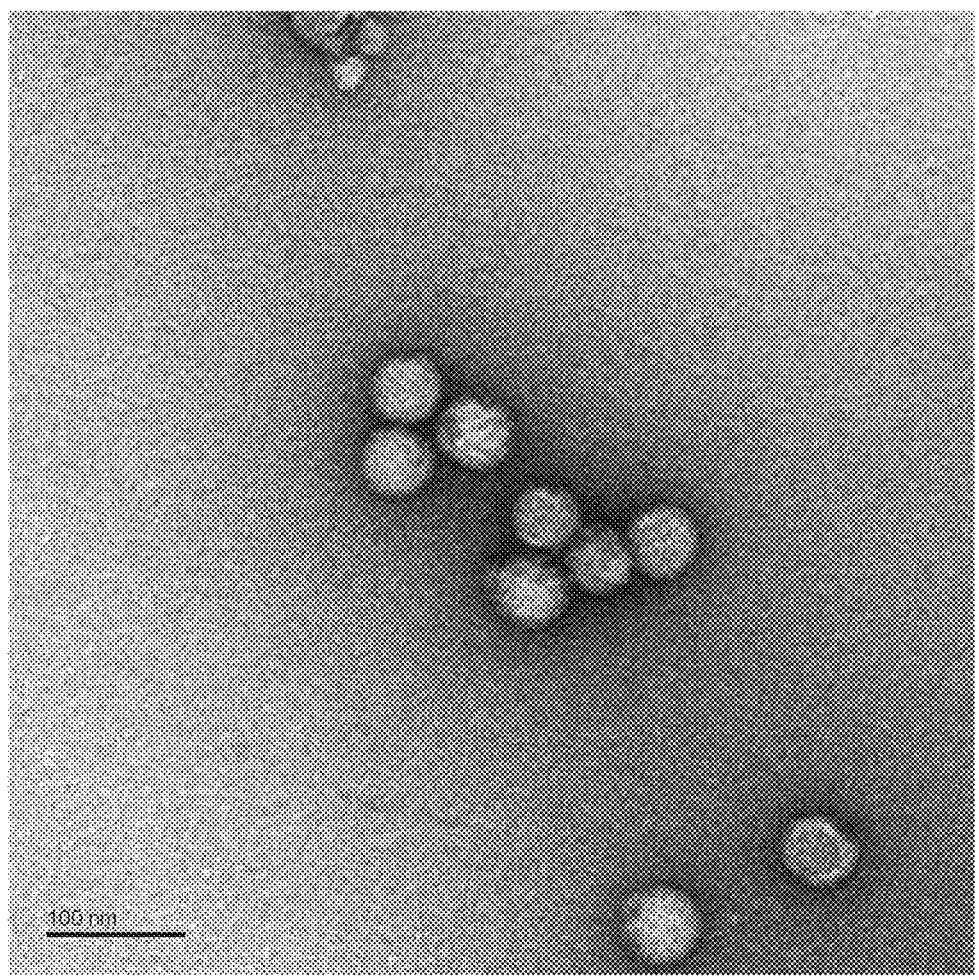
FIG. 4 is a photograph of fixed Japanese encephalitis virus particles photographed under an electron microscope (glutaraldehyde treatment).

In order to examine the shape of the EDC-fixed influenza virus particles in detail, observation under an electron microscope was carried out by the same method as in Example 2. As a representative, the photograph taken of the EDC-fixed influenza virus particles after reaction for 2 hours in an ice bath at an EDC concentration of 500 mM is shown in FIG. 3. The EDC-fixed influenza virus particles maintained the particle structure, and aggregates in which antigens were bound with each other were not observed.

3. Dynamic Light Scattering

The mean particle size of the EDC-fixed influenza virus particles was analyzed by using Zetasizer Nano ZS (manufactured by Malvern Panalytical Ltd.). The mean particle size in a liquid by the dynamic light scattering method is shown in Table 28. The EDC-fixed influenza virus particles (A/NY strain (strain of H3N2 subtype) and B/BR strain (strain of B type)) had a mean particle size around 130 to 160 nm which was single. From this, it was confirmed that the mean particle size of the EDC-fixed influenza virus particles is equivalent to the original virus particles. Namely, it was found that the mean particle size of the fixed influenza virus particles is single and is not variable even when EDC treatment is performed. The particle structure of the EDC-fixed influenza virus particles was maintained, and impurities such as aggregates were not observed.

TABLE 28

Mean particle size in liquid by dynamic light scattering method
(volume-weighted mean particle size (main peak) (nm))

| Strain name of original virus particles | EDC concentration (mM) | EDC-fixed influenza virus particles | Inactivated influenza virus particles |
|---|---|---|---|
| A/NY strain (strain of H3N2 subtype) | 50 | 159.0 | 159.2 |
| | 500 | 167.1 | |
| B/BR strain (strain of B type) | 50 | 136.3 | 137.8 |
| | 500 | 136.4 | |

4. Molecular Weight Distribution Measurement (SEC)

The molecular weight distribution of the EDC-fixed influenza virus particles originating in a strain of H3N2 subtype (A/NY strain) was measured. The measurement was performed by using size exclusion chromatography (trade name: TSKgel G6000PWXL (manufactured by Tosoh Corp.)) (performed at a flow rate of 0.5 ml/min by using PBS as an eluent). The elution pattern thereof is shown in Table 29. For the split flu antigen, four peaks were observed at an elution time around 16 to 30 minutes. On the other hand, for the EDC-fixed influenza virus particles, a single peak was observed at an elution time around 16 to 17 minutes

TABLE 29

SEC elution pattern (elution time (min))

| Strain name of original virus particles | Type of antigen | EDC concentration (mM) | EDC-fixed influenza virus particles |
|---|---|---|---|
| A/NY strain (strain of H3N2 subtype) | EDC-fixed influenza virus particles | 5 | 16-17 Single peak |
| | | 50 | 16-17 Single peak |
| | Split flu antigen | — | 16, 19, 26, 29 Four peaks |

5. Analysis by Degree of Cross-Linking

The degree of cross-linking of the EDC-fixed influenza virus particles prepared in Example 5 by the fixative was analyzed by the same method as in Example 2. The results about an A/NY strain (strain of H3N2 subtype) are shown in Table 30. The M1 protein residual rates (%) of the EDC-fixed influenza virus particles whose fixation was performed at EDC concentrations of 50 mM and 500 mM were 85.7% and 53.4%, respectively, showing that as the EDC concentration increases, cross-linking is accelerated so that the M1 protein residual rate decreases. The results about the B/BR strain (Victoria lineage strain of B type) are shown in Table 31. The M1 protein residual rates (%) of the EDC-fixed influenza virus particles whose fixation was performed at EDC concentrations of 5 mM, 50 mM, and 500 mM were 85.1%, 56.1%, and 27.2%, respectively. It was found that as the EDC concentration increases, cross-linking is accelerated so that the M1 protein residual rate decreases, as in the A/NY strain (strain of H3N2 subtype).

TABLE 30

A/NY strain (strain of H3N2 subtype): M1 protein residual rate

| | EDC concentration (mM) | M1 protein residual rate (%) |
|---|---|---|
| EDC-fixed influenza virus particles | 50 | 85.7 |
| | 500 | 53.4 |

TABLE 31

B/BR strain (Victoria lineage strain of B type): M1 protein residual rate

| | EDC concentration (mM) | M1 protein residual rate (%) |
|---|---|---|
| EDC-fixed influenza virus particles | 5 | 85.1 |
| | 50 | 56.1 |
| | 500 | 27.2 |

6. Immunogenicity (Mouse Intramuscular Inoculation)

The immunogenicity of the EDC-fixed influenza virus particles was evaluated by using mice. Serum was obtained by the same method as in Example 4, and the HI titer and the neutralizing titer were measured. As a representative, the results about the immunogenicity of the EDC-fixed influenza virus particles after reaction for 2 hours in an ice bath at EDC concentrations of 50 mM and 500 mM are shown in Table 32 (HI titer (GMT) for the A/NY strain), Table 33 (neutralizing titer (GMT) for the A/NY strain) and Table 34 (neutralizing titer (GMT) for the B/BR strain). In the case of the A/NY strain (strain of H3N2 subtype) and the B/BR strain (Victoria lineage strain of B type), the EDC-fixed influenza virus particles had significantly high immunogenicity as compared with the split flu antigen.

TABLE 32

HI titer (GMT): Immunogenicity (mouse intramuscular inoculation)

| | EDC concentration (mM) | EDC-fixed influenza virus particles | Split flu antigen |
|---|---|---|---|
| A/NY strain (strain of H3N2 subtype) | 50 | 24[*1] | 11 |
| | 500 | 44[*2] | |

[*1]$p < 0.05$,
[*2]$p < 0.01$

TABLE 33

Neutralizing titer (GMT): Immunogenicity (mouse intramuscular inoculation)

| | EDC concentration (mM) | EDC-fixed influenza virus particles | Split flu antigen |
|---|---|---|---|
| A/NY strain (strain of H3N2 subtype) | 50 | 1506[*1] | 682 |
| | 500 | 2201[*2] | |

[*1]$p < 0.01$,
[*2]$p < 0.001$

TABLE 34

Neutralizing titer (GMT): Immunogenicity (mouse intramuscular inoculation)

| | EDC concentration (mM) | EDC-fixed influenza virus particles | Split flu antigen |
|---|---|---|---|
| B/BR strain (Victoria lineage strain of B type) | 50 | 50 | 27 |
| | 500 | 87[*1] | |

[*1]$p < 0.01$

7. Antibody Subclass Analysis

The titers of virus antigen-specific IgG1 and IgG2a contained in the mouse serum obtained in "6. Immunogenicity (mouse intramuscular inoculation)" described above were measured by the ELISA method as antibody subclass analysis. As a result, it was shown that, in contrast to the split flu antigen, the EDC-fixed influenza virus particles induce antigen-specific IgG2a rather than antigen-specific IgG1 (Tables 35 and 36). From this result, the EDC-fixed influenza virus particles can be expected to further improve the efficacy of a vaccine as compared with the split flu antigen which activates humoral immunity but can hardly activate cell-mediated immunity.

TABLE 35

A/NY strain (strain of H3N2 subtype): Results of subclass analysis (EU/mL)

| IgG subclass | Split flu antigen | Inactivated influenza virus particles | EDC-fixed influenza virus particles | |
|---|---|---|---|---|
| | | | 500 mM | 50 mM |
| IgG1 | 4194 | 607 | 311 | 258 |
| IgG2a | 1518 | 25398 | 27194 | 34031 |

A value when the serum of each mouse immunized with the split flu antigen (IgG1) or virus-like particles (IgG2a) was diluted 25600-fold was defined as 1 EU/mL.

TABLE 36

B/BR strain (Victoria lineage strain of B type): Results of subclass analysis (EU/mL)

| IgG subclass | Split flu antigen | Inactivated influenza virus particles | EDC-fixed influenza virus particles | |
|---|---|---|---|---|
| | | | 500 mM | 50 mM |
| IgG1 | 3788 | 382 | 1069 | 1001 |
| IgG2a | 749 | 20306 | 25638 | 13471 |

A value when the serum of each mouse immunized with the split flu antigen (IgG1) or virus-like particles (IgG2a) was diluted 25600-fold was defined as 1 EU/mL.

8. Immunogenicity (Cynomolgus Monkey Subcutaneous Inoculation)

The immunogenicity of the EDC-fixed influenza virus particles was evaluated by using cynomolgus monkeys by the following procedures: first, the split flu antigen or the EDC-fixed influenza virus particles were subcutaneously inoculated at an inoculum dose of 15 μg as a HA content to cynomolgus monkeys (male or female, 29 to 35 months old) (8 animals per group). The subcutaneous inoculation was performed twice at a 3-week interval, and blood was collected at 4 weeks after the secondary immunization. Serum was obtained by the same method as in Example 2, and the HI titer and the neutralizing titer were measured. As a representative, the results about the HI titer (GMT) as the immunogenicity of the EDC-fixed influenza virus particles after reaction at 4° C. for 20 hours at an EDC concentration of 5 mM are shown in Table 37, and the results about the neutralizing titer (GMT) are shown in Table 38. For the A/CA strain (strain of H1N1 subtype), the A/NY strain (strain of H3N2 subtype), the B/MA strain (Yamagata lineage of B type), and the B/BR strain (Victoria lineage strain of B type), the EDC-fixed influenza virus particles had significantly high immunogenicity as compared with the split flu antigen.

TABLE 37

HI titer (GMT): Immunogenicity (cynomolgus monkey subcutaneous inoculation)

| | EDC-fixed influenza virus particles | Split flu antigen | Inactivated influenza virus particles |
|---|---|---|---|
| A/CA strain (strain of H1N1 subtype) | 174*[2] | 15 | 247*[2] |
| A/NY strain (strain of H3N2 subtype) | 48*[2] | 9 | 62*[2] |
| B/MA strain (Yamagata lineage strain of B type) | 20*[1] | 5 | 37*[2] |
| B/BR strain (Victoria lineage strain of B type) | 14*[1] | 5 | 24*[2] |

*[1] $p < 0.05$,
*[2] $p < 0.001$ (test of significant difference vs. split flu antigen)

TABLE 38

Neutralizing titer (GMT): Immunogenicity (cynomolgus monkey subcutaneous inoculation)

| | EDC-fixed influenza virus particles | Split flu antigen | Inactivated influenza virus particles |
|---|---|---|---|
| A/CA strain (strain of H1N1 subtype) | 640*[2] | 34 | 640*[2] |
| A/NY strain (strain of H3N2 subtype) | 494*[1] | 52 | 538*[2] |
| B/MA strain (Yamagata lineage strain of B type) | 67*[1] | 9 | 160*[2] |
| B/BR strain (Victoria lineage strain of B type) | 73*[1] | 10 | 174*[2] |

*[1] $p < 0.05$,
*[2] $p < 0.001$ (test of significant difference vs. split flu antigen)

9. Stability Before and after Stress Test (Analysis by Degree of Cross-Linking)

The stability of the EDC-fixed influenza virus particles prepared in Example 5 was evaluated by using change in the degree of cross-linking between before and after a stress test as an index. First, the M1 protein residual rate (%) was calculated by the same method as in Example 2, and the ratio of the M1 protein residual rate after the stress test at 37° C. for 1 week in the case of defining the M1 protein residual rate before the stress test as 100% was further calculated. The results about an A/NY strain (strain of H3N2 subtype) are shown in Table 39. The M1 protein residual rate after the stress test of the inactivated influenza virus particles increased by 24% as compared with before the stress test. On the other hand, the M1 protein residual rates after the stress test of the EDC-fixed influenza virus particles whose fixation was performed at EDC concentrations of 50 and 500 mM decreased by 18%, respectively, as compared with before the stress test, and the percent change was smaller than that of the inactivated influenza virus particles, suggesting being more stable.

TABLE 39

A/NY strain (strain of H3N2 subtype): Percent change in M1 protein residual rate between before and after stress test

| | EDC concentration (mM) | Percent change (%) in M1 protein residual rate between before and after stress test |
|---|---|---|
| EDC-fixed influenza virus particles | 50 | 18% decrease |
| | 500 | 18% decrease |
| Inactivated influenza virus particles | — | 24% increase |

10. Stability in Stress Test (Analysis by Single Radial Immunodiffusion Test)

The stability of the EDC-fixed influenza virus particles prepared in Example 5 was evaluated by using change in HA content between before and after a stress test as an index. First, the HA content was calculated by the single radial immunodiffusion test (Japanese Minimum Requirements for Biological Products (Ministry of Health, Labour and Welfare Ministerial Notification No. 192)), and the percent change in the HA content after the stress test at 37° C. for 1 week in the case of defining the HA content before the stress test as 100% was further calculated. The results about an A/CA strain (strain of H1N1 subtype), an A/NY strain (strain of H3N2 subtype), a B/MA strain (Yamagata lineage of B type), and a B/BR strain (Victoria lineage strain of B type) are shown in Table 40. The percent change in HA content after the stress test of the EDC-fixed influenza virus particles was small, suggesting being stable.

TABLE 40

Percent change in HA content of EDC-fixed influenza virus particles between before and after stress test

| | Percent change in HA content between before and after stress test |
|---|---|
| A/CA strain (strain of H1N1 subtype) | 8% decrease |
| A/NY strain (strain of H3N2 subtype) | 8% decrease |
| B/MA strain (Yamagata lineage strain of B type) | 7% decrease |
| B/BR strain (Victoria lineage strain of B type) | 10% decrease |

11. Stability Under Preservation at 5° C. for 11 Months (Analysis by Degree of Cross-Linking)

The stability of the EDC-fixed influenza virus particles prepared in Example 5 was evaluated by using change in the degree of cross-linking between before and after preservation at 5° C. for 11 months as an index. First, the M1 protein residual rate (%) was calculated by the same method as in Example 2, and the ratio of the M1 protein residual rate under the preservation at 5° C. for 11 months in the case of defining the M1 protein residual rate before the preservation at 5° C. for 11 months as 100% was further calculated. The results about an A/CA strain (strain of H1N1 subtype), an A/NY strain (strain of H3N2 subtype), a B/MA strain (Yamagata lineage of B type), and a B/BR strain (Victoria lineage strain of B type) are shown in Table 41. The percent change in the M1 protein residual rate under the preservation at 5° C. for 11 months of the EDC-fixed influenza virus particles was small, suggesting being stable.

TABLE 41

Percent change in M1 protein residual rate of EDC-fixed influenza virus particles after preservation at 5° C. for 11 months

| | Percent change in M1 protein residual rate after preservation at 5° C. for 11 months |
|---|---|
| A/CA strain (strain of H1N1 subtype) | 5% decrease |
| A/NY strain (strain of H3N2 subtype) | 9% decrease |
| B/MA strain (Yamagata lineage strain of B type) | 12% decrease |
| B/BR strain (Victoria lineage strain of B type) | 13% decrease |

12. Stability Under Preservation at 5° C. for 11 Months (Analysis by Single Radial Immunodiffusion Test)

The stability of the EDC-fixed influenza virus particles prepared in Example 5 was evaluated by using change in HA content between before and after preservation at 5° C. for 11 months as an index. First, the HA content was calculated by the single radial immunodiffusion test (Japanese Minimum Requirements for Biological Products (Ministry of Health, Labour and Welfare Ministerial Notification No. 192)), and the percent change in the HA content under the preservation at 5° C. for 11 months in the case of defining the HA content before the preservation at 5° C. for 11 months as 100% was further calculated. The results about an A/CA strain (strain of H1N1 subtype), an A/NY strain (strain of H3N2 subtype), a B/MA strain (Yamagata lineage of B type), and a B/BR strain (Victoria lineage strain of B type) are shown in Table 42. The percent change in HA content under the preservation at 5° C. for 11 months of the EDC-fixed influenza virus particles was small, suggesting being stable.

TABLE 42

Percent change in HA content of EDC-fixed influenza virus particles

| | Percent change in HA content |
|---|---|
| A/CA strain (strain of H1N1 subtype) | 1% decrease |
| A/NY strain (strain of H3N2 subtype) | 9% increase |
| B/MA strain (Yamagata lineage strain of B type) | 6% decrease |
| B/BR strain (Victoria lineage strain of B type) | 6% increase |

13. Stability Under Preservation at 5° C. for 9 Months (Mouse Immunogenicity (Intramuscular Inoculation))

The stability under preservation at 5° C. for 9 months of the EDC-fixed influenza virus particles prepared in Example 5 was evaluated by using mouse immunogenicity (intramuscular inoculation). Serum was obtained by the same method as in Example 4, and the HI titer and the neutralizing titer were measured. As a representative, the results about the HI titer (GMT) as the immunogenicity of the EDC-fixed influenza virus particles after reaction at 4° C. for 20 hours at an EDC concentration of 5 mM are shown in Table 43, and the results about the neutralizing titer (GMT) are shown in Table 44. For the A/CA strain (strain of H1N1 subtype), the A/NY strain (strain of H3N2 subtype), the B/MA strain (Yamagata lineage of B type), and the B/BR strain (Victoria lineage strain of B type), the EDC-fixed influenza virus particles had high immunogenicity as compared with the split flu antigen.

TABLE 43

HI titer (GMT): Immunogenicity (mouse intramuscular inoculation)

| | EDC-fixed influenza virus particles | Split flu antigen | Inactivated influenza virus particles |
|---|---|---|---|
| A/CA strain (strain of H1N1 subtype) | 53 | 28 | 61 |
| A/NY strain (strain of H3N2 subtype) | 15 | 13 | 14 |
| B/MA strain (Yamagata lineage strain of B type) | 30 | 20 | 32 |
| B/BR strain (Victoria lineage strain of B type) | 20 | 14 | 26 |

TABLE 44

Neutralizing titer (GMT): Immunogenicity (mouse intramuscular inoculation)

| | EDC-fixed influenza virus particles | Split flu antigen | Inactivated influenza virus particles |
|---|---|---|---|
| A/CA strain (strain of H1N1 subtype) | 640 | 279 | 640 |
| A/NY strain (strain of H3N2 subtype) | 1114 | 394 | 485 |
| B/MA strain (Yamagata lineage strain of B type) | 368 | 149 | 279 |
| B/BR strain (Victoria lineage strain of B type) | 75 | 40 | 86 |

14. Stability Under Preservation at 5° C. for 9 Months (Antibody Subclass)

The titers of virus antigen-specific IgG1 and IgG2a contained in the mouse serum obtained in "13. Stability under preservation at 5° C. for months (mouse immunogenicity (intramuscular inoculation))" described above were measured by the ELISA method as antibody subclass analysis. As a result, it was shown that, in contrast to the split flu antigen, the EDC-fixed influenza virus particles induce antigen-specific IgG2a rather than antigen-specific IgG1 (Table 45) even after the preservation at 5° C. for 9 months (Table 45). From this result, it can be expected that the cell-mediated immunity activated by the EDC-fixed influenza virus particles is maintained even after the preservation at 5° C. for 9 months.

TABLE 45

Results of IgG antibody subclass analysis (EU/mL)

| Vaccine strain | IgG subclass | EDC-fixed influenza virus particles | Split flu antigen | Inactivated influenza virus particles |
|---|---|---|---|---|
| A/CA | IgG1 | 572 | 6562 | 328 |
|  | IgG2a | 36333 | 11638 | 38237 |
| A/NY | IgG1 | 542 | 9393 | 666 |
|  | IgG2a | 18765 | 6726 | 15732 |
| B/MA | IgG1 | 881 | 4288 | 539 |
|  | IgG2a | 43141 | 7214 | 43339 |
| B/BR | IgG1 | 549 | 5403 | 532 |
|  | IgG2a | 13985 | 2657 | 21647 |

15. Stability Under Preservation at 5° C. for 10 Months (Cynomolgus Monkey Immunogenicity (Subcutaneous Inoculation))

The stability under preservation at 5° C. for 10 months of the EDC-fixed influenza virus particles prepared in Example 5 was evaluated by using cynomolgus monkey immunogenicity (subcutaneous inoculation). First, the split flu antigen, the EDC-fixed influenza virus particles, or the inactivated influenza virus particles were subcutaneously inoculated at an inoculum dose of 15 μg as a HA content to cynomolgus monkeys (male or female, 29 to 35 months old) (8 animals per group). The subcutaneous inoculation was performed twice at a 3-week interval, and blood was collected at 4 weeks after the secondary immunization. Serum was obtained by the same method as in Example 2, and the HI titer and the neutralizing titer were measured. As a representative, the results about the HI titer (GMT) under the preservation at 5° C. for 10 months of the EDC-fixed influenza virus particles after reaction at 4° C. for 20 hours at an EDC concentration of 5 mM are shown in Table 46, and the results about the neutralizing titer (GMT) are shown in Table 47 (Tables 46 and 47 reproduced Tables 37 and 38, respectively). For the A/CA strain (strain of H1N1 subtype), the A/NY strain (strain of H3N2 subtype), the B/MA strain (Yamagata lineage of B type), and the B/BR strain (Victoria lineage strain of B type), the EDC-fixed influenza virus particles had significantly high immunogenicity as compared with the split flu antigen.

TABLE 46

HI titer (GMT): Immunogenicity (cynomolgus monkey subcutaneous inoculation)

|  | EDC-fixed influenza virus particles | Split flu antigen | Inactivated influenza virus particles |
|---|---|---|---|
| A/CA strain (strain of H1N1 subtype) | 174[*2] | 15 | 247[*2] |
| A/NY strain (strain of H3N2 subtype) | 48[*2] | 9 | 62[*2] |
| B/MA strain (Yamagata lineage strain of B type) | 20[*1] | 5 | 37[*2] |
| B/BR strain (Victoria lineage strain of B type) | 14[*1] | 5 | 24[*2] |

[*1]$P < 0.05$,
[*2]$P < 0.001$ (test of significant difference vs. split flu antigen)

TABLE 47

Neutralizing titer (GMT): Immunogenicity (cynomolgus monkey subcutaneous inoculation)

|  | EDC-fixed influenza virus particles | Split flu antigen | Inactivated influenza virus particles |
|---|---|---|---|
| A/CA strain (strain of H1N1 subtype) | 640[*2] | 34 | 640[*2] |
| A/NY strain (strain of H3N2 subtype) | 494[*1] | 52 | 538[*2] |
| B/MA strain (Yamagata lineage strain of B type) | 67[*1] | 9 | 160[*2] |
| B/BR strain (Victoria lineage strain of B type) | 73[*1] | 10 | 174[*2] |

[*1]$P < 0.05$,
[*2]$P < 0.001$ (test of significant difference vs. split flu antigen)

16. Evaluation of Amount of RNA Released

The amount of RNA released over time during the protease treatment of the EDC-fixed influenza virus particles prepared in Example 5 was evaluated. First, the inactivated influenza virus particles and the EDC-fixed influenza virus particles were diluted with PBS, and SDS and proteinase K were added, and reacted at 55° C. while RNA was extracted over time. TRIzol LS Reagent, PureLink RNA Mini Kit, and PureLink DNase (manufactured by Invitrogen Corp., trade name) were used in the RNA extraction. The content of the extracted RNA was measured with Quant-iT RiboGreen RNA Reagent and Kit (manufactured by Invitrogen Corp., trade name). As a representative, the results about an A/NY strain (strain of H3N2 subtype) are shown in Table 48. As a result, it was shown that the RNA release of the EDC-fixed influenza virus particles is slowed as compared with the inactivated influenza virus particles.

TABLE 48

Time-dependent change in content of RNA released after protease treatment

| Protease treatment (hr) | RNA content (ng/mL) | |
|---|---|---|
|  | EDC-fixed influenza virus particles | Inactivated influenza virus particles |
| 0.1 | 828 | 4847 |
| 0.5 | 3151 | 5540 |
| 1.0 | 3640 | 6067 |
| 6.0 | 4681 | 6183 |
| 12.0 | 5654 | 5628 |
| 18.0 | 5250 | 5991 |

17. Evaluation of Amount of Inflammatory Cytokine Produced

The amounts of inflammatory cytokines produced over time against the EDC-fixed influenza virus particles prepared in Example 5 were evaluated. The method conformed to the European Pharmacopoeia Monocyte-Activation Test. Specifically, the human PBMC is used by pooling that from at least 4 donors in the European Pharmacopoeia Monocyte-Activation Test, but was changed to that from 1 donor and measured. Time-dependent change in the amount of IL-1β produced against the inactivated influenza virus particles and the EDC-fixed influenza virus particles of an A/NY strain (strain of H3N2 subtype) is shown in Table 49, and time-dependent change in the amount of IL-6 produced is shown in Table 50. Time-dependent change in the amount of IL-1β produced against the inactivated influenza virus particles and the EDC-fixed influenza virus particles of a B/BR strain (Victoria lineage strain of B type) is shown in Table 51, and time-dependent change in the amount of IL-6 produced is shown in Table 52. As a result, it was shown that the inflammatory cytokine production for the EDC-fixed influenza virus particles is slowed as compared with the inactivated influenza virus particles. Namely, it was suggested that RNA release in the body is slowed by EDC fixation to delay inflammatory cytokine production, whereby the EDC-fixed influenza virus particles have high safety.

TABLE 49

Time-dependent change in amount of IL-1β produced, released after PBMC stimulation (A/NY strain)

| Stimulation time (hr) | Amount of IL-1β produced (pg/mL) | |
|---|---|---|
| | EDC-fixed influenza virus particles | Inactivated influenza virus particles |
| 2.0 | 0 | 0 |
| 4.0 | 0 | 0 |
| 6.0 | 0 | 0 |
| 12.0 | 4.5 | 0 |
| 18.0 | 9.1 | 0 |
| 24.0 | 11.2 | 0 |
| 36.0 | 22.9 | 4.1 |
| 48.0 | 28.4 | 4.3 |

TABLE 50

Time-dependent change in amount of IL-6 produced, released after PBMC stimulation (A/NY strain)

| Stimulation time (hr) | Amount of IL-6 produced (pg/mL) | |
|---|---|---|
| | EDC-fixed influenza virus particles | Inactivated influenza virus particles |
| 2.0 | 0 | 0 |
| 4.0 | 0 | 0 |
| 6.0 | 0 | 0 |
| 12.0 | 28.3 | 14.1 |
| 18.0 | 65.7 | 20.5 |
| 24.0 | 135.3 | 29.2 |
| 36.0 | 240.3 | 37.7 |
| 48.0 | 321.3 | 46.4 |

TABLE 51

Time-dependent change in amount of IL-1β produced, released after PBMC stimulation (B/BR strain)

| Stimulation time (hr) | Amount of IL-1β produced (pg/mL) | |
|---|---|---|
| | EDC-fixed influenza virus particles | Inactivated influenza virus particles |
| 2.0 | 7.7 | 7.9 |
| 4.0 | 8.9 | 17.9 |
| 6.0 | 10.7 | 28.5 |
| 8.0 | 16.4 | 119.3 |
| 12.0 | 19.6 | 100.6 |
| 18.0 | 18.8 | 140.9 |
| 24.0 | 20.9 | 194.5 |
| 36.0 | 27.6 | 175.8 |
| 48.0 | 18.5 | 172.9 |

TABLE 52

Time-dependent change in amount of IL-6 produced, released after PBMC stimulation (B/BR strain)

| Stimulation time (hr) | Amount of IL-6 produced (pg/mL) | |
|---|---|---|
| | EDC-fixed influenza virus particles | Inactivated influenza virus particles |
| 2.0 | 32.4 | 46.7 |
| 4.0 | 152.2 | 477.6 |
| 6.0 | 200.9 | 548.6 |
| 8.0 | 226.0 | 547.1 |
| 12.0 | 304.1 | 693.0 |
| 18.0 | 311.6 | 740.7 |
| 24.0 | 331.5 | 780.8 |
| 36.0 | 304.1 | 645.6 |
| 48.0 | 292.3 | 599.1 |

Example 7

Preparation of GA-Fixed Japanese Encephalitis Virus Particles

1. Glutaraldehyde Treatment (Step of Fixing Particle Structure for Virus Particles)

Glutaraldehyde was added to a Vero cell culture Japanese encephalitis bulk vaccine (manufactured by General Incorporated Foundation, The Chemo-Sero-Therapeutic Research Institute, trade name "ENCEVAC", containing 60 to 90 μg/ml as a protein concentration of Japanese encephalitis virus particles already inactivated with 0.08 v/v % formalin; hereinafter, also referred to as "inactivated Japanese encephalitis virus particles") such that the final concentration became 0.005 to 0.02 w/v %, and reacted at 4° C. for 3 days. After the completion of reaction, the obtained reaction solution was dialyzed against a PBS-like solution (PBS supplemented with lactose (final concentration: 5 w/v %) which is an activator). Fixed Japanese encephalitis virus particles (hereinafter, also referred to as "GA-fixed Japanese encephalitis virus particles") were obtained by removing glutaraldehyde by dialysis. The pyrogenic activity of the obtained GA-fixed Japanese encephalitis virus particles was evaluated by a pyrogen test of evaluating the summed fever response of three rabbits, and the determination of the amount of an inflammatory cytokine produced in the case of stimulating human PBMC.

2. Pyrogen Test

The pyrogen test was conducted by the same method as in Example 1. One in which the protein content in 1 mL was adjusted to 70 μg by diluting the GA-fixed Japanese encephalitis virus particles or the inactivated Japanese encephalitis virus particles with saline was used as a sample. 3 mL of the sample per kg of body weight was inoculated to rabbits, and elevation in rectal temperature was observed up to 6 hours later. The summed fever response (° C.) of the three rabbits is shown in Table 53. As a representative, the GA-fixed Japanese encephalitis virus particles after reaction at 4° C. for 3 days at a glutaraldehyde concentration of 0.01 w/v % were evaluated.

For the GA-fixed Japanese encephalitis virus particles, a summed fever response of 1.3° C. or higher was not observed, and 1.6° C. or more decrease in summed fever response as compared with the inactivated Japanese encephalitis virus particles was seen. Also from this, it was suggested that the GA-fixed Japanese encephalitis virus particles have high safety.

TABLE 53

GA-fixed Japanese encephalitis virus particles:
Summed fever response of three rabbits

| | GA concentration (w/v %) | Summed fever response (° C.) |
|---|---|---|
| GA-fixed Japanese encephalitis virus particles | 0.01 | 0.94 |
| Inactivated Japanese encephalitis virus particles | — | 2.58 |

3. Determination of Amount of Inflammatory Cytokine Produced

The amounts of cytokines (IL-1β and IL-6) produced in the case of stimulating human PBMC with the GA-fixed Japanese encephalitis virus particles or the inactivated Japanese encephalitis virus particles were determined by a method conforming to the European Pharmacopoeia Monocyte-Activation Test. Specifically, the human PBMC is used by pooling that from at least 4 donors in the European Pharmacopoeia Monocyte-Activation Test, but was changed to that from 1 donor and measured. The results are shown in Table 54. It was found that the amounts of the inflammatory cytokines produced for the GA-fixed Japanese encephalitis virus particles are sufficiently lower than those for the inactivated Japanese encephalitis virus particles. Also from this, it was suggested that the GA-fixed Japanese encephalitis virus particles have higher safety than that of the inactivated Japanese encephalitis virus particles.

TABLE 54

| Amount of inflammatory cytokine produced | | | |
|---|---|---|---|
| | GA concentration (w/v %) | IL-1β (pg/mL) | IL-6 (pg/mL) |
| GA-fixed Japanese encephalitis virus particles | 0.005 | 4.7 | 10.5 |
| | 0.01 | 4.7 | 15.4 |
| | 0.02 | 0 | 14.8 |
| Inactivated Japanese encephalitis virus particles | — | 41.2 | 29.8 |

Example 8

Physical Evaluation

The physical properties of the GA-fixed Japanese encephalitis virus particles obtained in Example 7 described above were evaluated by the following methods.

1. Analysis Under Electron Microscope

In order to examine the shape of the GA-fixed Japanese encephalitis virus particles in detail, observation under an electron microscope was carried out by the same method as in Example 2. As a representative, the photograph taken of the GA-fixed Japanese encephalitis virus particles after reaction at 4° C. for 3 days at a glutaraldehyde concentration of 0.01 w/v % is shown in FIG. 4. The GA-fixed Japanese encephalitis virus particles maintained the particle structure by fixation in glutaraldehyde, as in the inactivated Japanese encephalitis virus particles.

2. Dynamic Light Scattering

The mean particle size of the GA-fixed Japanese encephalitis virus particles was analyzed by using Zetasizer Nano ZS (manufactured by Malvern Panalytical Ltd.). The mean particle size in a liquid by the dynamic light scattering method is shown in Table 55. The GA-fixed Japanese encephalitis virus particles had a mean particle size of approximately 90 nm which was single. On the other hand, the inactivated Japanese encephalitis virus particles were approximately 80 nm which was single. The particle structure of the GA-fixed Japanese encephalitis virus particles was maintained, and impurities such as aggregates were not observed.

TABLE 55

| Mean particle size in liquid by dynamic light scattering method | | |
|---|---|---|
| | GA concentration (w/v %) | Volume-weighted mean particle size (nm) |
| GA-fixed Japanese encephalitis virus particles | 0.005 | 92.9 |
| | 0.01 | 93.5 |
| | 0.02 | 95.1 |
| Inactivated Japanese encephalitis virus particles | — | 81.5 |

3. Molecular Weight Distribution Measurement (SEC)

The molecular weight distribution of the GA-fixed Japanese encephalitis virus particles was measured. The measurement was performed by using size exclusion chromatography (trade name: Superose 6 10/300 GE (manufactured by GE Healthcare Japan Corp.)) (performed at a flow rate of 0.5 ml/min by using PBS as an eluent). The elution pattern thereof is shown in Table 56. For the GA-fixed Japanese encephalitis virus particles, a single main peak was observed at an elution time around 14 to 15 minutes. For the inactivated Japanese encephalitis virus particles, a single main peak was also observed at an elution time around 14 to 15 minutes.

TABLE 56

| SEC elution pattern | | |
|---|---|---|
| | GA concentration (w/v %) | Elution time (min) |
| GA-fixed Japanese encephalitis virus particles | 0.005 | 14-15 Single peak |
| | 0.01 | 14-15 Single peak |
| | 0.02 | 14-15 Single peak |
| Inactivated Japanese encephalitis virus particles | — | 14-15 Single peak |

4. Content of Antigen

The content of an antigen (antigen content) was measured by the sandwich ELISA method using an anti-Japanese encephalitis virus antibody by the following procedures: E antigen contained in a specimen is captured to a microplate bound with anti-Japanese encephalitis virus rabbit IgG (primary antibody; polyclonal antibody). Then, an anti-Japanese encephalitis virus E protein monoclonal antibody (secondary antibody; monoclonal antibody) bound with horseradish-derived peroxide (HRP) is reacted so that a complex of plate-bound anti-E antigen antibody/E antigen/secondary antibody is formed. Unreacted remaining reagents and specimen are removed by washing, and HRP on the E antigen complex reacts by reacting with an enzyme substrate solution (o-phenylenediamine solution: OPD solution) so that color development occurs. The E antigen content (antigen content) was measured by utilizing the fact that the intensity of color development of OPD is parallel to the amount of the complex (which reflects the amount of the E antigen).

The respective antigen contents of the GA-fixed Japanese encephalitis virus particles and the inactivated Japanese encephalitis virus particles are shown in Table 57. As a representative, when the GA-fixed Japanese encephalitis virus particles after reaction at 4° C. for 3 days at a glutaraldehyde concentration of 0.01 w/v % were evaluated, the antigen equivalent to the inactivated Japanese encephalitis virus particles was contained.

TABLE 57

Results about antigen content

|  | GA concentration (w/v %) | Antigen content (μg/mL) |
|---|---|---|
| GA-fixed Japanese encephalitis virus particles | 0.01 | 74.5 |
| Inactivated Japanese encephalitis virus particles | — | 74.0 |

5. Analysis by Specific Activity

The degree of cross-linking by the fixative was evaluated by specific activity (antigen content/protein content) as to the GA-fixed Japanese encephalitis virus particles prepared in Example 7. Specifically, a monoclonal antibody (503) that is used in the measurement of the antigen content recognizes a neutralizing epitope, and the specific activity decreases when the structural change of the neutralizing epitope occurs. A relative value (%) of the specific activity (hereinafter, this relative value is also referred to as a "503 antibody response rate" (%)) of the GA-fixed Japanese encephalitis virus particles treated at each glutaraldehyde concentration to the specific activity of the unfixed inactivated Japanese encephalitis virus particles was calculated. The results are shown in Table 58. The 503 antibody response rates of the GA-fixed Japanese encephalitis virus particles whose fixation was performed at glutaraldehyde concentrations of 0.005 w/v %, 0.01 w/v %, and 0.02 w/v % were 95.1%, 74.7%, and 55.2%, respectively, suggesting that as the glutaraldehyde concentration increases, cross-linking is accelerated so that the response rate decreases by the structural change of the 503 antibody epitope.

TABLE 58

GA-fixed Japanese encephalitis virus particles: 503 antibody response rate

|  | GA concentration (w/v %) | 503 antibody response rate (%) |
|---|---|---|
| GA-fixed Japanese encephalitis virus particles | 0.005 | 95.1 |
|  | 0.01 | 74.7 |
|  | 0.02 | 55.2 |

6. Immunogenicity (Mouse Intraperitoneal Inoculation)

As a representative, the GA-fixed Japanese encephalitis virus particles after reaction 4° C. for 3 days at a glutaraldehyde concentration of 0.005 or 0.01 w/v % or the inactivated Japanese encephalitis virus particles were intraperitoneally inoculated at an inoculum dose of 1 μg or 0.25 μg to ddY mice (female, 4 weeks old) (10 animals per group). One week after the immunization, immunization was performed again, and 1 week thereafter, the mice were subjected to the collection of whole blood and euthanized. Serum was obtained by centrifugation and pooled in an equal amount among the groups, and the neutralizing titer was measured according to "Pathogen Detection Manual" (edited by National Institute of Infectious Diseases, Japan). The results calculated from 50% plaque reduction are shown in Table 59. The GA-fixed Japanese encephalitis virus particles had an equivalent or higher neutralizing titer as compared with the inactivated Japanese encephalitis virus particles.

TABLE 59

Results about immunogenicity (neutralizing titer)

|  | GA concentration (w/v %) | Inoculum dose (μg) | |
|---|---|---|---|
|  |  | 1 | 0.25 |
| GA-fixed Japanese encephalitis virus particles | 0.005 | $10^{2.3}$ | $10^{1.7}$ |
|  | 0.01 | $10^{3.2}$ | $10^{1.8}$ |
| Inactivated Japanese encephalitis virus particles | — | $10^{2.3}$ | $10^{1.6}$ |

7. Stability in Acceleration Test (Antigen Content)

The GA-fixed Japanese encephalitis virus particles and the inactivated Japanese encephalitis virus particles were diluted with a PBS-like solution such that the final protein concentration became 8 μg/mL. The preservation stability at 25° C. was evaluated with an antigen content as an index. As a representative, the results about the GA-fixed Japanese encephalitis virus particles after reaction at 4° C. for 3 days at a glutaraldehyde concentration of 0.01 w/v % or the inactivated Japanese encephalitis virus particles are shown in Table 60. The GA-fixed Japanese encephalitis virus particles maintained the antigen content for 1 month under preservation at 25° C. On the other hand, the inactivated Japanese encephalitis virus particles exhibited decrease under preservation at 25° C. It was shown that the GA-fixed Japanese encephalitis virus particles are improved in stability as compared with the inactivated Japanese encephalitis virus particles.

TABLE 60

Results about stability (antigen content (μg/mL))

|  | GA concentration (w/v %) | 25° C. | |
|---|---|---|---|
|  |  | Day 0 | 1 month later |
| GA-fixed Japanese encephalitis virus particles | 0.01 | 6.9 (100) | 6.5 (94.2) |
| Inactivated Japanese encephalitis virus particles | — | 8.9 (100) | 6.7 (75.3) |

Rate of change (%) in antigen content when the antigen content on day 0 was defined as 100% is shown within the parentheses.

8. Stability in Acceleration Test (Dynamic Light Scattering)

The GA-fixed Japanese encephalitis virus particles and the inactivated Japanese encephalitis virus particles were diluted with a PBS-like solution such that the final protein concentration became 8 μg/mL. The preservation stability at 25° C. was evaluated with a mean particle size in a liquid by the dynamic light scattering method using Zetasizer Nano ZS, as an index. As a representative, the results about the GA-fixed Japanese encephalitis virus particles after reaction at 4° C. for 3 days at a glutaraldehyde concentration of 0.01 w/v % or the inactivated Japanese encephalitis virus particles are shown in Table 61. The GA-fixed Japanese encephalitis virus particles maintained the mean particle size for 1 month under preservation at 25° C. On the other hand, the inactivated Japanese encephalitis virus particles exhibited increase under preservation at 25° C. It was thereby shown that the GA-fixed Japanese encephalitis virus particles are improved in stability as compared with the inactivated Japanese encephalitis virus particles.

TABLE 61

Results about stability (volume-weighted mean particle size (nm))

| | GA concentration (w/v %) | 25° C. | |
|---|---|---|---|
| | | Day 0 | 1 month later |
| GA-fixed Japanese encephalitis virus particles | 0.01 | 89.9 (100) | 88.9 (98.2) |
| Inactivated Japanese encephalitis virus particles | — | 87.3 (100) | 125.5 (143.8) |

Rate of change (%) in mean particle size when the mean particle size on day 0 was defined as 100% is shown within the parentheses.

9. Stability Under Preservation at 4° C. (Immunogenicity)

The GA-fixed Japanese encephalitis virus particles and the inactivated Japanese encephalitis virus particles were diluted with a PBS-like solution such that the final protein concentration became 8 μg/mL. The preservation stability at 4° C. was evaluated with immunogenicity (neutralizing titer) in mice as an index. As a representative, the results about the GA-fixed Japanese encephalitis virus particles after reaction at 4° C. for 15 months at a glutaraldehyde concentration of 0.01 w/v % or the inactivated Japanese encephalitis virus particles are shown in Table 62. Although the dose differed between 0 months and 15 months later, it was considered that the GA-fixed Japanese encephalitis virus particles maintain the immunogenicity for 15 months under preservation at 4° C. On the other hand, it was considered that the inactivated Japanese encephalitis virus particles exhibited decrease under preservation at 4° C. It was considered that the GA-fixed Japanese encephalitis virus particles are improved in stability as compared with the inactivated Japanese encephalitis virus particles.

TABLE 62

Results about immunogenicity (neutralizing titer)

| | GA concentration (w/v %) | 4° C. | | | |
|---|---|---|---|---|---|
| | | 0 months | | 15 months later | |
| | | Dose | | | |
| | | 1 | 0.25 | 0.8 | 0.2 |
| GA-fixed Japanese encephalitis virus particles | 0.01 | $10^{3.4}$ | $10^{2.1}$ | $10^{3.1}$ | $10^{2.2}$ |
| Inactivated Japanese encephalitis virus particles | — | $10^{3.5}$ | $10^{2.1}$ | $10^{2.1}$ | $10^{1.0}$ |

Example 9

Preparation of FA-Fixed Japanese Encephalitis Virus Particles

1. Formalin Treatment (Step of Fixing Particle Structure for Virus Particles)

Formalin (36 to 38 w/v % aqueous formaldehyde solution) was added to the inactivated Japanese encephalitis virus particles such that the final concentration became 0.014 to 0.04 v/v % (0.005 to 0.015 w/v % in terms of formaldehyde), and reacted at 25° C. for 1 week. After the completion of reaction, formalin was removed by dialyzing the reaction solution against a PBS-like solution, to thereby obtain fixed Japanese encephalitis virus particles (hereinafter, also referred to as "FA-fixed Japanese encephalitis virus particles"). The pyrogenic activity of the obtained FA-fixed Japanese encephalitis virus particles was evaluated by the determination of the amount of an inflammatory cytokine produced in the case of stimulating human PBMC.

2. Determination of Amount of Inflammatory Cytokine Produced

The amounts of cytokines (IL-1β and IL-6) produced in the case of stimulating human PBMC with the FA-fixed Japanese encephalitis virus particles or the inactivated Japanese encephalitis virus particles were determined by a method conforming to the European Pharmacopoeia Monocyte-Activation Test. Specifically, the human PBMC is used by pooling that from at least 4 donors in the European Pharmacopoeia Monocyte-Activation Test, but was changed to that from 1 donor and measured. The results are shown in Table 63. It was found that the amounts of the inflammatory cytokines produced for the FA-fixed Japanese encephalitis virus particles are sufficiently lower than those for the inactivated Japanese encephalitis virus particles. Also from this, it was suggested that the FA-fixed Japanese encephalitis virus particles have higher safety than that of the inactivated Japanese encephalitis virus particles.

TABLE 63

Amount of inflammatory cytokine produced

| | Formalin concentration (v/v %) | IL-1β (pg/mL) | IL-6 (pg/mL) |
|---|---|---|---|
| FA-fixed Japanese encephalitis virus particles | 0.014 | 4.0 | 16.4 |
| | 0.02 | 0 | 16.4 |
| | 0.04 | 4.0 | 18.1 |
| Inactivated Japanese encephalitis virus particles | — | 41.2 | 29.8 |

Example 10

Physical Evaluation

The physical properties of the FA-fixed Japanese encephalitis virus particles obtained in Example 9 described above were evaluated by the following methods.

1. Analysis Under Electron Microscope

Figure 5:
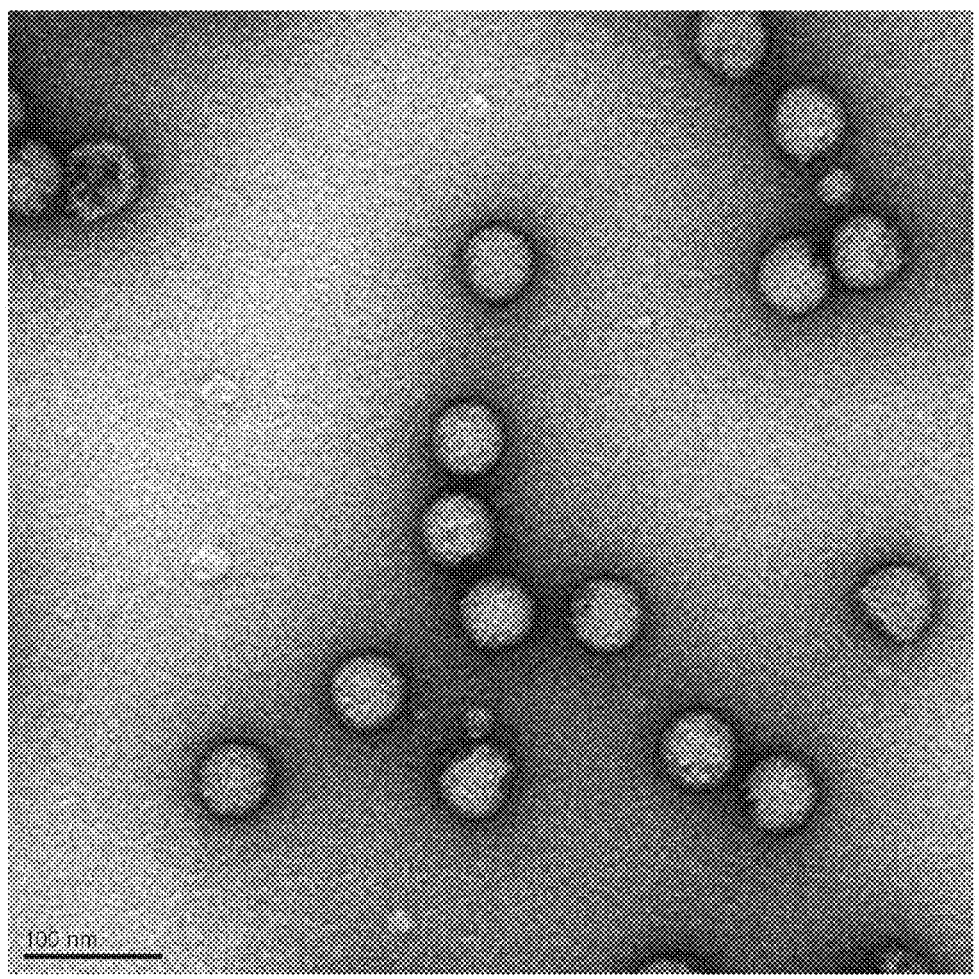
FIG. 5 is a photograph of fixed Japanese encephalitis virus particles photographed under an electron microscope (formalin treatment).

In order to examine the shape of the FA-fixed Japanese encephalitis virus particles in detail, observation under an electron microscope was carried out by the same method as in Example 2. As a representative, the photograph taken of the FA-fixed Japanese encephalitis virus particles after reaction at 25° C. for 1 week at a formalin concentration of 0.014 v/v % is shown (FIG. 5). The FA-fixed Japanese encephalitis virus particles maintained the particle structure by fixation in formalin, as in the inactivated Japanese encephalitis virus particles.

2. Dynamic Light Scattering

The mean particle size of the FA-fixed Japanese encephalitis virus particles was analyzed by using Zetasizer Nano ZS (manufactured by Malvern Panalytical Ltd.). The mean particle size in a liquid by the dynamic light scattering method is shown in Table 64. The FA-fixed Japanese encephalitis virus particles had a mean particle size of approximately 90 nm which was single. On the other hand, the inactivated Japanese encephalitis virus particles were approximately 80 nm which was single. The particle structure of the FA-fixed Japanese encephalitis virus particles was maintained, and impurities such as aggregates were not observed.

TABLE 64

Mean particle size in liquid by dynamic light scattering method

| | Formalin concentration (v/v %) | Volume-weighted mean particle size (nm) |
|---|---|---|
| FA-fixed Japanese encephalitis virus particles | 0.014 | 92.0 |
| | 0.02 | 92.3 |
| | 0.04 | 93.9 |
| Inactivated Japanese encephalitis virus particles | — | 81.5 |

3. Molecular Weight Distribution Measurement (SEC)

The molecular weight distribution of the FA-fixed Japanese encephalitis virus particles was measured by the same method (SEC) as in Example 8. The elution pattern is shown in Table 65. For the FA-fixed Japanese encephalitis virus particles, a single main peak was observed at an elution time around 14 to 15 minutes. For the inactivated Japanese encephalitis virus particles, a single main peak was also observed at an elution time around 14 to 15 minutes.

TABLE 65

SEC elution pattern

| | Formalin concentration (v/v %) | Elution time (min) |
|---|---|---|
| FA-fixed Japanese encephalitis virus particles | 0.014 | 14-15 Single peak |
| | 0.02 | 14-15 Single peak |
| | 0.04 | 14-15 Single peak |
| Inactivated Japanese encephalitis virus particles | — | 14-15 Single peak |

4. Content of Antigen

The content of an antigen (antigen content) was measured by the sandwich ELISA method using an anti-Japanese encephalitis virus antibody by the same method as in Example 8.

The respective antigen contents of the FA-fixed Japanese encephalitis virus particles and the inactivated Japanese encephalitis virus particles are shown in Table 66. As a representative, when the FA-fixed Japanese encephalitis virus particles after reaction at 25° C. for 1 week at formalin concentrations of 0.014 v/v % and 0.02 v/v % were evaluated, the antigen equivalent to the inactivated Japanese encephalitis virus particles was contained.

TABLE 66

Results about antigen content

| | Formalin concentration (v/v %) | Antigen content (μg/mL) |
|---|---|---|
| FA-fixed Japanese encephalitis virus particles | 0.014 | 85.9 |
| | 0.02 | 65.5 |
| Inactivated Japanese encephalitis virus particles | — | 74.0 |

5. Immunogenicity (Mouse Intraperitoneal Inoculation)

As a representative, the neutralizing titer of the FA-fixed Japanese encephalitis virus particles after reaction 25° C. for 1 week at a formalin concentration of 0.02 v/v % was measured by the same method as in Example 8. The results calculated from 50% plaque reduction are shown in Table 67. The FA-fixed Japanese encephalitis virus particles had an equivalent or higher neutralizing titer as compared with the inactivated Japanese encephalitis virus particles.

TABLE 67

Results about immunogenicity (neutralizing titer)

| | Formalin concentration (v/v %) | Inoculum dose (μg) 0.25 |
|---|---|---|
| FA-fixed Japanese encephalitis virus particles | 0.02 | $10^{1.2}$ |
| Inactivated Japanese encephalitis virus particles | — | $10^{<1}$ |

6. Stability in Stress Test (Antigen Content)

The FA-fixed Japanese encephalitis virus particles and the inactivated Japanese encephalitis virus particles were diluted with a PBS-like solution such that the final protein concentration became 8 μg/mL. The preservation stability at 37° C. was evaluated with an antigen content as an index. As a representative, the results after reaction at 25° C. for 1 week at a formalin concentration of 0.014 v/v % are shown in Table 68. The FA-fixed Japanese encephalitis virus particles maintained the antigen content for 1 week under preservation at 37° C. On the other hand, the inactivated Japanese encephalitis virus particles exhibited decrease under preservation at 37° C. It was shown that the FA-fixed Japanese encephalitis virus particles are improved in stability as compared with the inactivated Japanese encephalitis virus particles.

TABLE 68

Results about stability (antigen content (μg/mL))

| | Formalin concentration (v/v %) | 37° C. | |
|---|---|---|---|
| | | Day 0 | 1 week later |
| FA-fixed Japanese encephalitis virus particles | 0.014 | 5.3 (100) | 5.4 (102.7) |
| Inactivated Japanese encephalitis virus particles | — | 8.6 (100) | 6.3 (73.3) |

Rate of change (%) in antigen content when the antigen content on day 0 was defined as 100% is shown within the parentheses.

Example 11

Preparation of EDC-Fixed Japanese Encephalitis Virus Particles 1. 1-Ethyl-3-(3-Dimethylaminopropyl)Carbodiimide Hydrochloride (EDC) Treatment EDC was added to the inactivated Japanese encephalitis virus particles such that the final concentration became 0.15 to 15 mM, and reacted at 4° C. for 2 to 20 hours. In the case of performing quenching treatment, glycine was further added as a quencher in 8 times the amount of EDC (molar mass ratio) to the reaction solution. After the completion of reaction, EDC and glycine were removed by dialyzing the reaction solution against a PBS-like solution, to thereby obtain fixed Japanese encephalitis virus particles (hereinafter, also referred to as "EDC-fixed Japanese encephalitis virus particles"). The pyrogenic activity of the obtained EDC-fixed Japanese encephalitis virus particles was evaluated by the determination of the amount of an inflammatory cytokine produced in the case of stimulating human PBMC.

2. Determination of Amount of Inflammatory Cytokine Produced

As a representative, the amounts of cytokines (IL-1β and IL-6) produced in the case of stimulating human PBMC with the EDC-fixed Japanese encephalitis virus particles after reaction at 4° C. for 20 hours at an EDC concentration of 0.15 mM or 1.5 mM or the inactivated Japanese encephalitis virus particles were determined by a method conforming to the European Pharmacopoeia Monocyte-Activation Test. Specifically, the human PBMC is used by pooling that from at least 4 donors in the European Pharmacopoeia Monocyte-Activation Test, but was changed to that from 1 donor and measured. The results are shown in Table 69. It was found that the amounts of the inflammatory cytokines produced for the EDC-fixed Japanese encephalitis virus particles are sufficiently lower than those for the inactivated Japanese encephalitis virus particles. Also from this, it was suggested that the EDC-fixed Japanese encephalitis virus particles have higher safety than that of the inactivated Japanese encephalitis virus particles.

TABLE 69

Amount of inflammatory cytokine produced

| | EDC concentration (mM) | Quenching treatment | IL-1β (pg/mL) | IL-6 (pg/mL) |
|---|---|---|---|---|
| EDC-fixed Japanese encephalitis virus particles | 0.15 | Not performed | 8.3 | 19.2 |
| | 1.5 | Not performed | 8.7 | 17.5 |
| Inactivated Japanese encephalitis virus particles | — | — | 41.2 | 29.8 |

Example 12

Physical Evaluation

The physical properties of the EDC-fixed Japanese encephalitis virus particles obtained in Example 11 described above were evaluated by the following methods.

1. Analysis Under Electron Microscope

Figure 6:
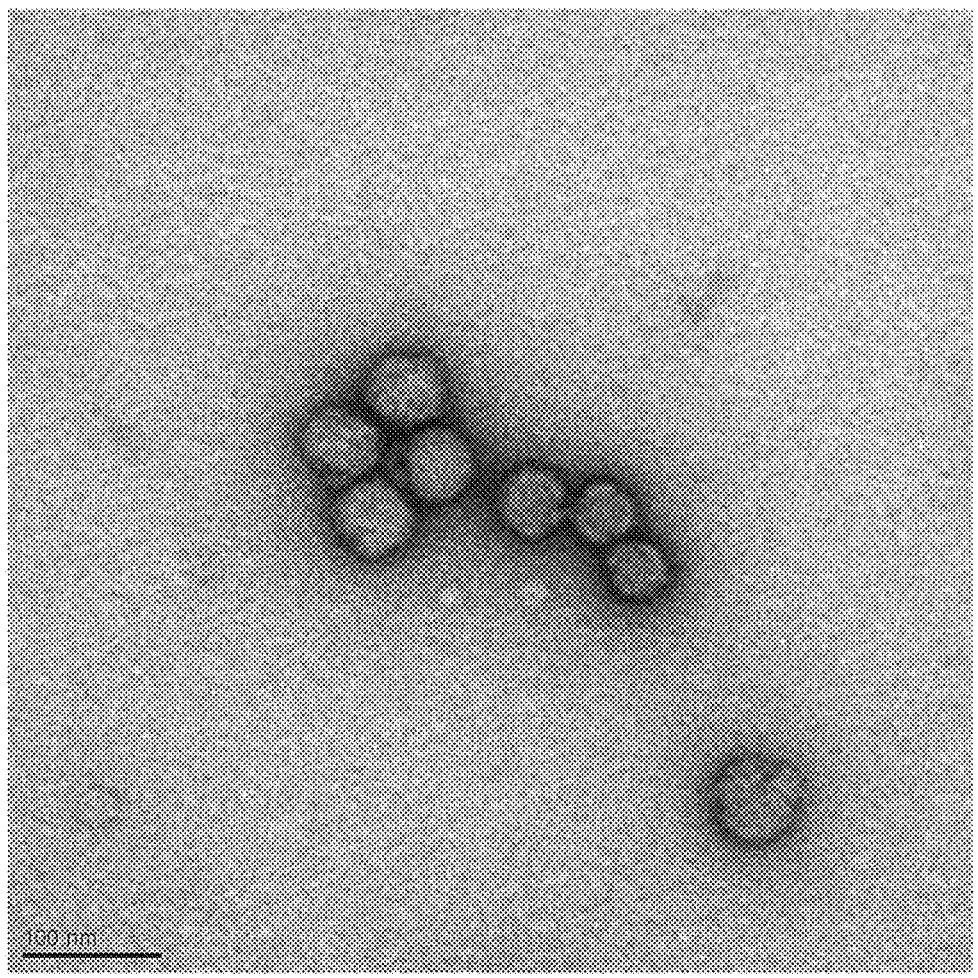
FIG. 6 is a photograph of fixed Japanese encephalitis virus particles photographed under an electron microscope (EDC treatment).

In order to examine the shape of the EDC-fixed Japanese encephalitis virus particles in detail, observation under an electron microscope was carried out by the same method as in Example 2. As a representative, the photograph taken of the EDC-fixed Japanese encephalitis virus particles after reaction at 4° C. for 20 hours at an EDC concentration of 1.5 mM is shown in FIG. 6. The EDC-fixed Japanese encephalitis virus particles maintained the particle structure by fixation in EDC, as in the inactivated Japanese encephalitis virus particles.

2. Dynamic Light Scattering

The mean particle size of the EDC-fixed Japanese encephalitis virus particles was analyzed by using Zetasizer Nano ZS (manufactured by Malvern Panalytical Ltd.). The mean particle size in a liquid by the dynamic light scattering method is shown in Table 70. The EDC-fixed Japanese encephalitis virus particles had a mean particle size of approximately 90 nm which was single. On the other hand, the inactivated Japanese encephalitis virus particles were approximately 80 nm which was single. The particle structure of the EDC-fixed Japanese encephalitis virus particles was maintained, and impurities such as aggregates were not observed.

TABLE 70

Mean particle size in liquid by dynamic light scattering method

| | EDC concentration (mM) | Quenching treatment | Volume-weighted mean particle size (nm) |
|---|---|---|---|
| EDC-fixed Japanese encephalitis virus particles | 0.15 | Not performed | 91.9 |
| | 1.5 | Not performed | 91.8 |
| | | Performed | 91.8 |
| | 15 | Not performed | 94.0 |
| Inactivated Japanese encephalitis virus particles | — | — | 81.5 |

3. Molecular Weight Measurement (SEC)

The molecular weight distribution of the EDC-fixed Japanese encephalitis virus particles was measured by the same method as in Example 8. The elution pattern is shown in Table 71. For the EDC-fixed Japanese encephalitis virus particles, a single main peak was observed at an elution time around 14 to 15 minutes. For the inactivated Japanese encephalitis virus particles, a single main peak was also observed at an elution time around 14 to 15 minutes.

TABLE 71

SEC elution pattern

| | EDC concentration (mM) | Quenching treatment | Elution time (min) |
|---|---|---|---|
| EDC-fixed Japanese encephalitis virus particles | 0.15 | Not performed | 14-15 Single peak |
| | 1.5 | Not performed | 14-15 Single peak |
| | | Performed | 14-15 Single peak |
| | 15 | Not performed | 14-15 Single peak |
| Inactivated Japanese encephalitis virus particles | — | — | 14-15 Single peak |

4. Content of Antigen

The content of an antigen (antigen content) was measured by the sandwich ELISA method using an anti-Japanese encephalitis virus antibody by the same method as in Example 8. As a representative, the respective antigen contents of the EDC-fixed Japanese encephalitis virus particles after reaction at 4° C. for 20 hours at an EDC concentration of 1.5 mM and the inactivated Japanese encephalitis virus particles are shown in Table 72. The EDC-fixed Japanese encephalitis virus particles contained the antigen equivalent to the inactivated Japanese encephalitis virus particles.

TABLE 72

Results about antigen content

| | EDC concentration (mM) | Quenching treatment | Antigen content (μg/mL) |
|---|---|---|---|
| EDC-fixed Japanese encephalitis virus particles | 1.5 | Not performed | 78.5 |
| Inactivated Japanese encephalitis virus particles | — | — | 74.0 |

5. Immunogenicity (Mouse Intraperitoneal Inoculation)

The neutralizing titer of the EDC-fixed Japanese encephalitis virus particles was measured by the same method as in Example 8. The results calculated from 50% plaque reduction are shown in Table 73. As a representative, when the EDC-fixed Japanese encephalitis virus particles in which after reaction at 4° C. for 2 hours at an EDC concentration of 1.5 mM, glycine was added as a quencher in 8 times the amount of EDC (molar mass ratio) to the reaction solution were evaluated, the neutralizing titer was equivalent or higher as compared with the inactivated Japanese encephalitis virus particles.

TABLE 73

Results about immunogenicity (neutralizing titer)

| | EDC concentration (mM) | Quenching treatment | Inoculum dose (μg) 1 |
|---|---|---|---|
| EDC-fixed Japanese encephalitis virus particles | 1.5 | Performed | $10^{2.6}$ |
| Inactivated Japanese encephalitis virus particles | — | — | $10^{2.3}$ |

6. Stability (Antigen Content)

The EDC-fixed Japanese encephalitis virus particles and the inactivated Japanese encephalitis virus particles were diluted with a PBS-like solution such that the final protein concentration became 8 μg/mL. The preservation stability at 25° C. or 37° C. was evaluated with an antigen content as an index. The results are shown in Tables 74 and 75. The EDC-fixed Japanese encephalitis virus particles maintained the antigen content for 1 month under preservation at 25° C. and for 1 week under preservation at 37° C. On the other hand, the inactivated Japanese encephalitis virus particles exhibited decrease in antigen content both under preservation at 25° C. and under preservation at 37° C. It was shown that the EDC-fixed Japanese encephalitis virus particles are improved in stability as compared with the inactivated Japanese encephalitis virus particles.

TABLE 74

Results about stability (antigen content (μg/mL))

| | EDC concentration (mM) | Quenching treatment | 25° C. | |
|---|---|---|---|---|
| | | | Day 0 | 1 month later |
| EDC-fixed Japanese encephalitis virus particles | 0.15 | Not performed | 8.8 (100) | 7.4 (83.4) |
| | 1.5 | Not performed | 8.7 (100) | 7.7 (88.6) |
| | 15 | Not performed | 7.1 (100) | 7.1 (100) |
| Inactivated Japanese encephalitis virus particles | — | — | 8.6 (100) | 6.8 (78.9) |

Rate of change (%) in antigen content when the antigen content on day 0 was defined as 100% is shown within the parentheses.

TABLE 75

Results about stability (antigen content (μg/mL))

| | EDC concentration (mM) | Quenching treatment | 37° C. | |
|---|---|---|---|---|
| | | | Day 0 | 1 week later |
| EDC-fixed Japanese encephalitis virus | 0.15 | Not performed | 6.6 (100) | 5.8 (85.3) |
| | 1.5 | Not performed | 6.6 (100) | 6.0 (90.9) |

TABLE 75-continued

Results about stability (antigen content (μg/mL))

| | EDC concentration (mM) | Quenching treatment | 37° C. Day 0 | 1 week later |
|---|---|---|---|---|
| particles | | Performed | 5.8 (100) | 5.8 (100) |
| Inactivated Japanese encephalitis virus particles | — | — | 7.2 (100) | 5.1 (70.8) |

Rate of change (%) in antigen content when the antigen content on day 0 was defined as 100% is shown within the parentheses.

INDUSTRIAL APPLICABILITY

The present invention is useful in the field of pharmaceuticals, particularly, in the field of vaccines.

The invention claimed is:

1. A vaccine containing fixed virus particles,
wherein the fixed virus particles are obtained by treating original virus particles or corresponding inactivated virus particles with a fixative,
wherein the fixative comprises glutaraldehyde or 1-ethyl-3-(3-dimethylaminopropyl) carbodiimide hydrochloride,
wherein the virus particles comprise influenza virus particles or Japanese encephalitis virus particles, and
wherein a summed fever response of three rabbits to the fixed virus particles in a pyrogen test is less than 80% based on a summed fever response of three rabbits to the original virus particles of the fixed virus particles or the corresponding inactivated virus particles.

2. The vaccine according to claim 1, wherein the summed fever response of three rabbits to the fixed virus particles in the pyrogen test is 1.3° C. or lower.

3. A vaccine containing fixed virus particles,
wherein the fixed virus particles are obtained by treating original virus particles or corresponding inactivated virus particles with a fixative,
wherein the fixative comprises glutaraldehyde or 1-ethyl-3-(3-dimethylaminopropyl) carbodiimide hydrochloride,
wherein the virus particles comprise influenza virus particles or Japanese encephalitis virus particles, and
wherein an amount of an inflammatory cytokine produced from human peripheral blood mononuclear cells stimulated with the fixed virus particles is less than 80% based on an amount of the inflammatory cytokine produced from human peripheral blood mononuclear cells stimulated with original virus particles of the fixed virus particles or corresponding inactivated virus particles.

4. The vaccine according to claim 1, wherein the influenza virus particles comprise influenza A virus particles or influenza B virus particles.

5. The vaccine according to claim 1, wherein the influenza virus particles comprise influenza virus particles classified into a strain of H1N1 subtype, a strain of H2N2 subtype, a strain of H3N2 subtype, a strain of H3N8 subtype, a strain of H5N1 subtype, a strain of H5N2 subtype, a strain of H5N6 subtype, a strain of H6N1 subtype, a strain of H7N3 subtype, a strain of H7N7 subtype, a strain of H7N9 subtype, a strain of H9N2 subtype, or a strain of H10N8 subtype.

6. The vaccine according to claim 1, wherein the Japanese encephalitis virus particles comprise a Beijing-1 strain, a Nakayama strain, a SA14-14-2 strain, or a P3 strain.

7. The vaccine according to claim 1, wherein 0% to 90% of a surface protein on the fixed virus particles is unfixed.

8. The vaccine according to claim 1, wherein a relative value of specific activity (antigen content/protein content) of the fixed virus particles to specific activity of the original virus particles of the fixed virus particles is 0 to 95%.

9. The vaccine according to claim 1, wherein the fixed virus particles have a mean particle size of 80% to 150% of particle sizes of the original virus particles of the fixed virus particles or the corresponding inactivated virus particles.

10. The vaccine according to claim 1, wherein a peak is detected at a sucrose concentration of 35% or higher when the fixed virus particles are measured by sucrose density gradient cocentrifugation.

11. The vaccine according to claim 1, wherein a single peak is observed when the fixed virus particles are measured by high-performance liquid chromatography.

12. The vaccine according to claim 1, wherein the vaccine induces the fixed virus particle-specific IgG2a rather than the fixed virus particle-specific IgG1 when immunizing a mouse.

13. A method for producing fixed virus particles, comprising the step of adding a fixative to a suspension containing original virus particles or corresponding inactivated virus particles,
wherein the fixative comprises glutaraldehyde or 1-ethyl-3-(3-dimethylaminopropyl) carbodiimide hydrochloride, and
wherein the virus particles comprise influenza virus particles or Japanese encephalitis virus particles.

14. The production method according to claim 13, wherein a concentration of the glutaraldehyde is 0.001 to 0.06 w/v % based on the total amount of the suspension and the fixative.

15. The production method according to claim 13, wherein a concentration of the 1-ethyl-3-(3-dimethylaminopropyl)carbodiimide hydrochloride is 0.05 to 1500 mM based on the total amount of the suspension and the fixative.

16. The production method according to claim 13, wherein the original virus particles are virus particles recovered by infecting cultured cells, a chicken egg or the mouse brain.

17. The production method according to claim 16, wherein the cultured cells comprise primary cells or cell lines.

18. The production method according to claim 17, wherein the cultured cells comprise Vero cells or MDCK cells.

19. A method for producing a vaccine, comprising the step of adding the fixed virus particles obtained by a production method according to claim 13 with at least one selected from the group consisting of a pharmaceutically acceptable carrier, an emulsifier, a preservative, a tonicity agent, a pH adjuster, and an inactivator, thereby producing the vaccine.

* * * * *